US011955230B2

(12) United States Patent
Davis

(10) Patent No.: US 11,955,230 B2
(45) Date of Patent: Apr. 9, 2024

(54) REMOTE DATA ANALYSIS AND DIAGNOSIS

(71) Applicant: Beckman Coulter, Inc., Brea, CA (US)

(72) Inventor: Martha C. Davis, Brea, CA (US)

(73) Assignee: Beckman Coulter, Inc., Brea, CA (US)

( * ) Notice: Subject to any disclaimer, the term of this patent is extended or adjusted under 35 U.S.C. 154(b) by 76 days.

(21) Appl. No.: 17/539,440

(22) Filed: Dec. 1, 2021

(65) Prior Publication Data

US 2022/0093244 A1   Mar. 24, 2022

Related U.S. Application Data

(63) Continuation of application No. 16/330,338, filed as application No. PCT/US2017/049083 on Aug. 29, 2017, now Pat. No. 11,195,611.

(Continued)

(51) Int. Cl.
| | | |
|---|---|---|
| *G16H 40/40* | (2018.01) | |
| *G06F 8/65* | (2018.01) | |
| *G06F 16/2457* | (2019.01) | |
| *G16H 10/40* | (2018.01) | |
| *G16H 40/67* | (2018.01) | |
| *G06F 21/62* | (2013.01) | |
| *H04L 9/40* | (2022.01) | |

(52) U.S. Cl.
CPC ............... *G16H 40/40* (2018.01); *G06F 8/65* (2013.01); *G06F 16/24578* (2019.01); *G16H 10/40* (2018.01); *G16H 40/67* (2018.01); *G06F 21/6245* (2013.01); *H04L 63/029* (2013.01); *H04L 63/0428* (2013.01)

(58) Field of Classification Search
CPC ............................. G16H 40/67; G16H 40/40
See application file for complete search history.

(56) References Cited

U.S. PATENT DOCUMENTS

| | | | |
|---|---|---|---|
| 4,858,154 A | 8/1989 | Anderson et al. | |
| 5,532,941 A | 7/1996 | Lin | |

(Continued)

FOREIGN PATENT DOCUMENTS

| | | |
|---|---|---|
| CN | 1530817 A | 9/2004 |
| CN | 101286954 A | 10/2008 |

(Continued)

OTHER PUBLICATIONS

Said, Hisham, et al. "Utilizing Telematics Data to Support Effective Equipment Fleet-Management Decisions: Utilization Rate and Hazard Functions." (Year: 2015).*

(Continued)

*Primary Examiner* — Jason B Dunham
*Assistant Examiner* — Constantine Siozopoulos
(74) *Attorney, Agent, or Firm* — Frost Brown Todd LLP

(57) ABSTRACT

Described herein are database systems including one or more remote analytical instruments operably connected to one or more servers. The instruments can transmit rich data to the servers, and the one or more servers can compile a database of the rich data. One or more processors associated with the servers can be configured to execute a data analytics program on the database to identify a stochastic phenomenon or to process the data and present in real-time at a location of the one or more instruments comparison information about the instruments.

22 Claims, 31 Drawing Sheets

Related U.S. Application Data

(60) Provisional application No. 62/380,749, filed on Aug. 29, 2016.

(56) References Cited

U.S. PATENT DOCUMENTS

| | | |
|---|---|---|
| 5,946,471 A | 8/1999 | Voorhees |
| 6,192,320 B1 | 2/2001 | Margrey et al. |
| 6,269,276 B1 | 7/2001 | Akhavan et al. |
| 6,434,572 B2 | 8/2002 | Derzay et al. |
| 6,574,518 B1 | 6/2003 | Lounsberry et al. |
| 6,629,060 B2 | 9/2003 | Okuno et al. |
| 6,937,964 B2 | 8/2005 | Okuno et al. |
| 7,403,873 B2 | 7/2008 | Okuno et al. |
| 7,606,680 B2 | 10/2009 | Okuno et al. |
| 7,661,013 B2 | 2/2010 | Berman et al. |
| 7,680,605 B2 | 3/2010 | Yung et al. |
| 7,725,297 B2 | 5/2010 | Okuno et al. |
| 7,761,809 B2 | 7/2010 | Bukovec |
| 8,065,113 B2 | 11/2011 | Okuno et al. |
| 8,230,041 B2 | 7/2012 | Minowa et al. |
| 8,626,149 B2 | 1/2014 | Steenstra |
| 9,342,807 B2 | 5/2016 | Yamaguchi et al. |
| 9,407,861 B2 | 8/2016 | Huenerfauth et al. |
| 9,443,710 B2 | 9/2016 | Platt et al. |
| 9,842,295 B2 | 12/2017 | Fisher |
| 9,935,852 B2 | 4/2018 | Nasgowitz et al. |
| 9,952,659 B2 | 4/2018 | Joseph et al. |
| 10,197,993 B2 | 2/2019 | Lesher |
| 10,431,335 B2 | 10/2019 | Cork et al. |
| 10,739,362 B2 | 8/2020 | Goemann |
| 11,195,611 B2 | 12/2021 | Davis |
| 11,199,557 B2 | 12/2021 | Parker et al. |
| 2004/0034478 A1 | 2/2004 | Yung et al. |
| 2004/0042471 A1 | 3/2004 | Yung et al. |
| 2004/0130572 A1 | 7/2004 | Bala |
| 2005/0038676 A1 | 2/2005 | Showalter et al. |
| 2005/0106736 A1 | 5/2005 | Yung et al. |
| 2005/0143956 A1 | 6/2005 | Long et al. |
| 2006/0074597 A1 | 4/2006 | Raphael et al. |
| 2006/0206358 A1 | 9/2006 | Beaver |
| 2006/0292642 A1 | 12/2006 | Khosravi et al. |
| 2007/0129894 A1 | 6/2007 | Yung |
| 2007/0196909 A1 | 8/2007 | Showalter et al. |
| 2009/0313347 A1 | 12/2009 | Engel et al. |
| 2010/0127885 A1 | 5/2010 | Okuno et al. |
| 2010/0229022 A1 | 9/2010 | Anand et al. |
| 2011/0245089 A1 | 10/2011 | Scott et al. |
| 2012/0041777 A1 | 2/2012 | Case et al. |
| 2012/0290104 A1 | 11/2012 | Holt et al. |
| 2013/0014012 A1 | 1/2013 | Boucher et al. |
| 2014/0184223 A1* | 7/2014 | Otvos ............... G01R 33/307 324/318 |
| 2014/0282181 A1 | 9/2014 | Declerck |
| 2015/0127270 A1 | 5/2015 | Goemann-Thoss et al. |
| 2015/0213192 A1 | 7/2015 | Patel et al. |
| 2016/0018347 A1 | 1/2016 | Drbal et al. |
| 2016/0292393 A1 | 10/2016 | Balwani |
| 2016/0356801 A1 | 12/2016 | Glavina et al. |
| 2017/0017538 A1 | 1/2017 | Rudorfer et al. |
| 2019/0146466 A1 | 5/2019 | Lesher |
| 2019/0376991 A1* | 12/2019 | Rudorfer .......... G01N 35/00623 |
| 2020/0185091 A1 | 6/2020 | Davis |
| 2020/0382599 A1 | 12/2020 | Knafel et al. |
| 2020/0411176 A1 | 12/2020 | Hadorn et al. |
| 2021/0081839 A1 | 3/2021 | Heydlauf |
| 2022/0208364 A1 | 6/2022 | Naik et al. |

FOREIGN PATENT DOCUMENTS

| | | |
|---|---|---|
| CN | 101926156 B | 12/2010 |
| CN | 102867013 A | 1/2013 |
| CN | 107271650 A | 10/2017 |
| CN | 109314650 A | 2/2019 |
| EP | 0353591 B1 | 4/1996 |
| EP | 1437648 A2 | 1/2006 |
| EP | 1779317 A1 | 5/2007 |
| EP | 1965326 A2 | 9/2008 |
| EP | 1107159 B1 | 4/2009 |
| EP | 2243285 A1 | 10/2010 |
| EP | 2544131 A1 | 1/2013 |
| EP | 2756294 A1 | 7/2014 |
| EP | 2778994 A1 | 9/2014 |
| EP | 3140761 A1 | 3/2017 |
| EP | 3226002 A1 | 10/2017 |
| EP | 3033594 A1 | 3/2018 |
| EP | 3465984 A1 | 4/2019 |
| EP | 3533065 A1 | 9/2019 |
| JP | 2004-213677 | 2/2007 |
| JP | 2017-187473 | 10/2017 |
| WO | WO 2003/010612 A2 | 2/2003 |
| WO | WO 2007/087136 A2 | 8/2007 |
| WO | WO 2009/079558 A1 | 6/2009 |
| WO | WO 2010/086862 A1 | 8/2010 |
| WO | WO-2010099170 A1 * | 9/2010 ............ G06F 11/008 |
| WO | WO 2011/067559 A1 | 6/2011 |
| WO | WO-2011067559 A1 * | 6/2011 ........... C12Q 1/6869 |
| WO | WO 2013/039772 A1 | 3/2013 |
| WO | WO 2015/023443 A1 | 2/2015 |
| WO | WO 2015/171581 A1 | 11/2015 |
| WO | WO 2015/179370 A1 | 11/2015 |
| WO | WO 2017/214030 A1 | 12/2017 |
| WO | WO 2018/081617 A2 | 5/2018 |
| WO | WO 2019/216975 A1 | 11/2019 |
| WO | WO 2020/223616 A2 | 11/2020 |

OTHER PUBLICATIONS

Chinese Office Action dated Nov. 11, 2022 for Application No. 201780060693.5, 12 pages.
European Office Action dated Feb. 24, 2021 for Application No. 17765515.6, 7 pages.
European Examination Report dated Jul. 16, 2021 for Application No. 17798039.8, 8 pages.
Indian First Examination Report dated Jun. 29, 2021 for Application No. 201947012118, 5 pages.
International Search Report and Written Opinion dated Nov. 27, 2017 for International Application No. PCT/US2017/049083, 23 pages.
International Search Report and Written Opinion dated Jan. 30, 2018 for International Application No. PCT/US2017/058467, 14 pages.
Berman, P. et al. "Tight Approximability Results for Test Set Problems in Bioinformatics", Algorithm Theory—SWAT 2004. Publication [online]. Jun. 2004 [retrieved Apr. 17, 2023] Retrieved from the Internet: <URL: https://www.researchgate.net/profile/Bhaskar_Dasgupta3/publication/225344842_Tight_Approximability_Results_for_Test_Set_Problems_in_Bioinformatics/links/02bfe5107204a21054000000/Tight-Approximability-Results-for-Test-Set-Problems-in-Bioinformatics.pdf><DOI:10.1007/978-3-540-27810-8_5>.
Munoz, Miguel A., et al. "Context-aware mobile communication in hospitals." *Computer* 36.9 (2003): 38-46, 9 pages.
U.S. Non-Final Rejection dated Sep. 29, 2020 for U.S. Appl. No. 16/330,338, 18 pages.
U.S. Ex Parte Quayle Office Action dated Jun. 15, 2021, for U.S. Appl. No. 16/396,186, 18 pages.

* cited by examiner

FIG. 8

| Assay | 3419 | 3457 | 3491 | 3503 | 4066 | 4071 | 3569 | 3587 |
|---|---|---|---|---|---|---|---|---|
| AMPH | 176 | 303 | 562 | 28 | 148 | 205 | 437 | 494 |
| AMY7 | 100 | 277 | 361 | 162 | 336 | 341 | 540 | 521 |
| AST- | 959 | 1457 | 2394 | 949 | 1725 | 2168 | 8626 | 8694 |
| BARB | 167 | 297 | 546 | 26 | 169 | 201 | 423 | 475 |
| BNZG | 165 | 313 | 554 | 34 | 140 | 195 | 427 | 474 |
| BUN | 1639 | 4813 | 5891 | 1790 | 4377 | 5109 | 440 | 480 |
| CAR | --- | 16 | 268 | 96 | 156 | 188 | --- | 257 |
| CHOL | 127 | 580 | 481 | 160 | 526 | 540 | 4106 | 4116 |
| CK | 467 | 349 | 413 | 402 | 1135 | 1275 | 946 | 874 |
| COCM | 153 | 302 | 553 | 28 | 151 | 225 | 436 | 486 |
| CR-S | 1639 | 4696 | 5742 | 1764 | 3722 | 4488 | --- | --- |
| CRPH | 145 | 363 | 507 | | 303 | 314 | 997 | 966 |
| DBIL | 291 | 622 | 725 | 259 | 666 | 655 | 1341 | 1202 |
| DIGN | --- | 241 | 266 | 124 | 369 | 391 | 328 | 305 |
| FE | --- | 18 | 410 | 112 | --- | --- | --- | 2313 |
| GEN | --- | 97 | 245 | 93 | 53 | 36 | --- | 262 |
| GGT | 71 | 225 | 228 | --- | 317 | --- | 628 | --- |
| GLU | 1656 | 4635 | 5654 | 1714 | 3549 | 4226 | 16842 | 16672 |
| HDLD | 139 | 508 | 409 | 153 | 470 | 513 | 4070 | 4087 |
| LD | 118 | 347 | 554 | 109 | 460 | 413 | 703 | 876 |
| LDLD | --- | --- | --- | --- | --- | --- | 235 | --- |
| LI | --- | 288 | 289 | 47 | 288 | 21 | 304 | --- |
| LIP | 239 | 499 | 773 | 239 | 734 | 623 | 841 | 817 |
| M-TP | 24 | 176 | 260 | 165 | 192 | 222 | 629 | 862 |
| MA | --- | --- | --- | --- | --- | --- | 680 | 697 |
| METD | --- | --- | --- | --- | --- | --- | --- | 317 |
| METQ | --- | --- | --- | --- | --- | --- | --- | 318 |
| MG | 468 | 1425 | 1781 | 586 | 1527 | 1650 | 4370 | 4408 |
| OP | 164 | 321 | 583 | 28 | 146 | 211 | 431 | 498 |
| PAB | 145 | 375 | 461 | 178 | 437 | 500 | 533 | 549 |
| PCP | 155 | 327 | 559 | 28 | 142 | 205 | 428 | 473 |
| PHE | --- | 16 | 251 | 97 | | 342 | 245 | --- |
| PHS | 166 | 919 | 1229 | 291 | 565 | 542 | 211 | 209 |
| PHY | --- | 16 | 248 | 106 | 353 | 356 | 282 | 275 |
| SALY | 191 | 347 | 542 | 103 | 459 | 465 | 238 | 280 |
| TBIL | 1063 | 1595 | 2657 | 1025 | 1835 | 2259 | 8664 | 8784 |
| TG | 149 | 609 | 501 | 193 | 497 | 553 | 4155 | 4182 |
| THC5 | 187 | 315 | 563 | 28 | 138 | 210 | 436 | 483 |
| THE | --- | 18 | 232 | 5 | --- | 344 | --- | 234 |
| TOB | --- | 16 | 222 | --- | --- | --- | --- | 197 |
| TP | 970 | 1462 | 2405 | 954 | 1744 | 2156 | --- | --- |
| TRFN | --- | --- | --- | --- | --- | --- | --- | 2159 |
| UDR | --- | 33 | 292 | 48 | --- | 78 | 647 | 205 |
| URIC | 121 | 337 | 427 | 222 | 429 | 450 | 991 | 1000 |
| VANC | --- | 296 | 296 | 124 | 490 | 448 | 360 | 331 |
| VPA | --- | 45 | 395 | 120 | 410 | 426 | 302 | 308 |

FIG. 18

Customer Analytics Sample Report -
Service Records Overview Trigger Service Requests

| formation | Assay Count | Assay Count Breakdown | Assay Count Site Comparison | Tests Per Cartridge | QC Testing Overview | Calibration Dates | Cross Site Menu | Service Records Overview |
|---|---|---|---|---|---|---|---|---|

This view can be used to find information on service calls during the selected date range.

Calls in the Trigger column are initiated by the service provider to the customer based on data gathered from the instrument(s).

Use the following menus to select desired parameters. Use the "Ctrl" key to make multiple selections on dropdown menus.

IDN
- ☐ Entity A
- ☐ Entity B
- ☐ Entity C
- ☑ ENTITY D

SITE
- ☐ Atlanta
- ☐ Harbor City
- ☐ Los Angeles
- ☑ ONTARIO
- ☐ Pasadena City

INSTRUMENT TYPE
- ☐ DXC
- ☑ DXH

☐ Servie Record

| IDN | SITE | SN | DATE | TRIGGER | SR TYPE | SR # | PART # | INSTRUMENT TYPE |
|---|---|---|---|---|---|---|---|---|
| ENTITY D | ONTARIO | AT09327 | 9/24/2014 | AMS-CTS-CBC background high | &-Telephone $ | 22739385 | 629029 | DXH |
| ENTITY D | ONTARIO | AT09327 | 9/24/2014 | AMS-CTS-CBC background high | &-Telephone $ | 22739385 | 629029 | DXH |
| ENTITY D | ONTARIO | AT09327 | 9/24/2014 | AMS-CTS-CBC background high | &-Telephone $ | 22739385 | 629029 | DXH |
| ENTITY D | ONTARIO | AT09327 | 9/24/2014 | AMS-CTS-CBC background high | &-Telephone $ | 22739385 | 629029 | DXH |
| ENTITY D | ONTARIO | AT09327 | 9/24/2014 | AMS-CTS-CBC background high | &-Telephone $ | 22739385 | 629029 | DXH |
| ENTITY D | ONTARIO | AT09327 | 9/24/2014 | AMS-CTS-Latron Out of range | &-Telephone $ | 22739385 | 629029 | DXH |
| ENTITY D | ONTARIO | AT09327 | 9/24/2014 | AMS-CTS-CBC background high | &-Telephone $ | 22739385 | 629029 | DXH |

☐ Response Details

| SR # | FOLLOWUP DATE | FOLLOWUP DETAILS | | SR TYPE |
|---|---|---|---|---|
| 22739385 | 6/27/14 | CTS-Latron Out Latron near or out of range 3 Times in 2 Days. Troubleshoot Advisor K25752315 & K14914615 Please us | | &-Telephone |

REMOTE DATA ANALYSIS AND DIAGNOSIS

CROSS REFERENCE TO RELATED APPLICATIONS

This application is a continuation of U.S. non-provisional patent application Ser. No. 16/330,338, entitled "Remote Data Analysis and Diagnosis," filed Mar. 4, 2019, which is the national stage entry of international patent application PCT/US17/49083, entitled "Remote Data Analysis and Diagnosis," filed Aug. 29, 2017, which claims the benefit of, U.S. provisional patent application 62/380,749, titled "Remote Data Analysis and Diagnosis," filed on Aug. 29, 2016, the disclosures of which are hereby incorporated by reference in their entirety for all purposes.

FIELD

This disclosure relates to processing rich data and presenting analysis in real time using a suite of applications for remotely coupled laboratory instruments.

BACKGROUND

Identifying and diagnosing issues with complex tools, such as laboratory instruments, can be difficult. This is especially true where issues may arise from stochastic phenomenon, as these may not be evident from analyzing data from a single instrument. While detecting such phenomenon may be possible, doing so could require gathering large amounts of rich data from multiple instruments. This may present various logistical and security challenges, and could also present challenges related to working with the data even after it has been collected (e.g., how to accommodate the fact that the volume of data may exceed the constraints of available bandwidth and/or memory for use in analyzing it). Accordingly, there is a need for technology which can address issues related to identifying and diagnosing issues with complex tools, especially in a context where large volumes of data are involved in such identification and/or diagnosis.

SUMMARY

Embodiments described herein generally are database systems that transmit data from one or more instruments to one or more servers that compile a database including rich data from the instruments. The servers may be configured to analyze the rich data using an analytics program or a module that may be configured to perform analytics to display real-time or near real-time result of the analysis. In this context, "rich data" should be understood as data which may be associated with metadata that allows it to be correlated with other data when neither the rich data nor the other data with which it would be correlated directly refers to or explicitly incorporates the other. As an example of "rich data", a measurement stored in a database with metadata indicating a serial number of the instrument, which took the measurement that would allow the measurement to be compared against measurements taken by other instruments purchased by the same customer using a customer database that correlated instrument serial numbers with customers

BRIEF DESCRIPTION OF THE DRAWINGS

FIGS. 3-8 are screenshots of exemplary embodiments of various applications produced from database systems such as FIGS. 1, 2A, 2B and 9.

FIGS. 18-19 are exemplary interfaces which present calibration information to a user.

FIGS. 22-23 are exemplary interfaces which present service history information to a user.

Figure 29:
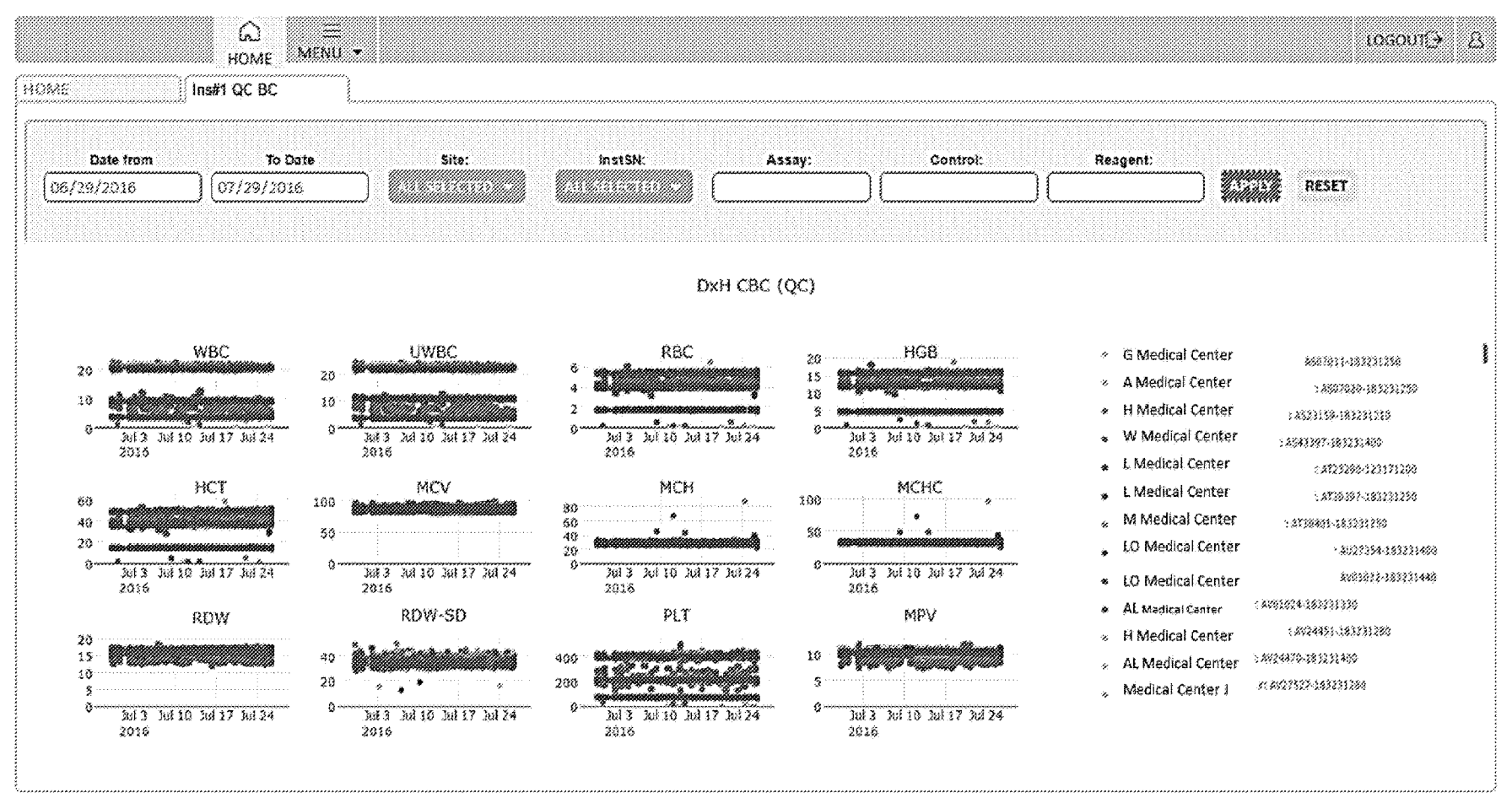

FIG. 29 is an exemplary interface of a peer comparison of QC control charts of different blood components and parameters.

DETAILED DESCRIPTION

Figure 1:
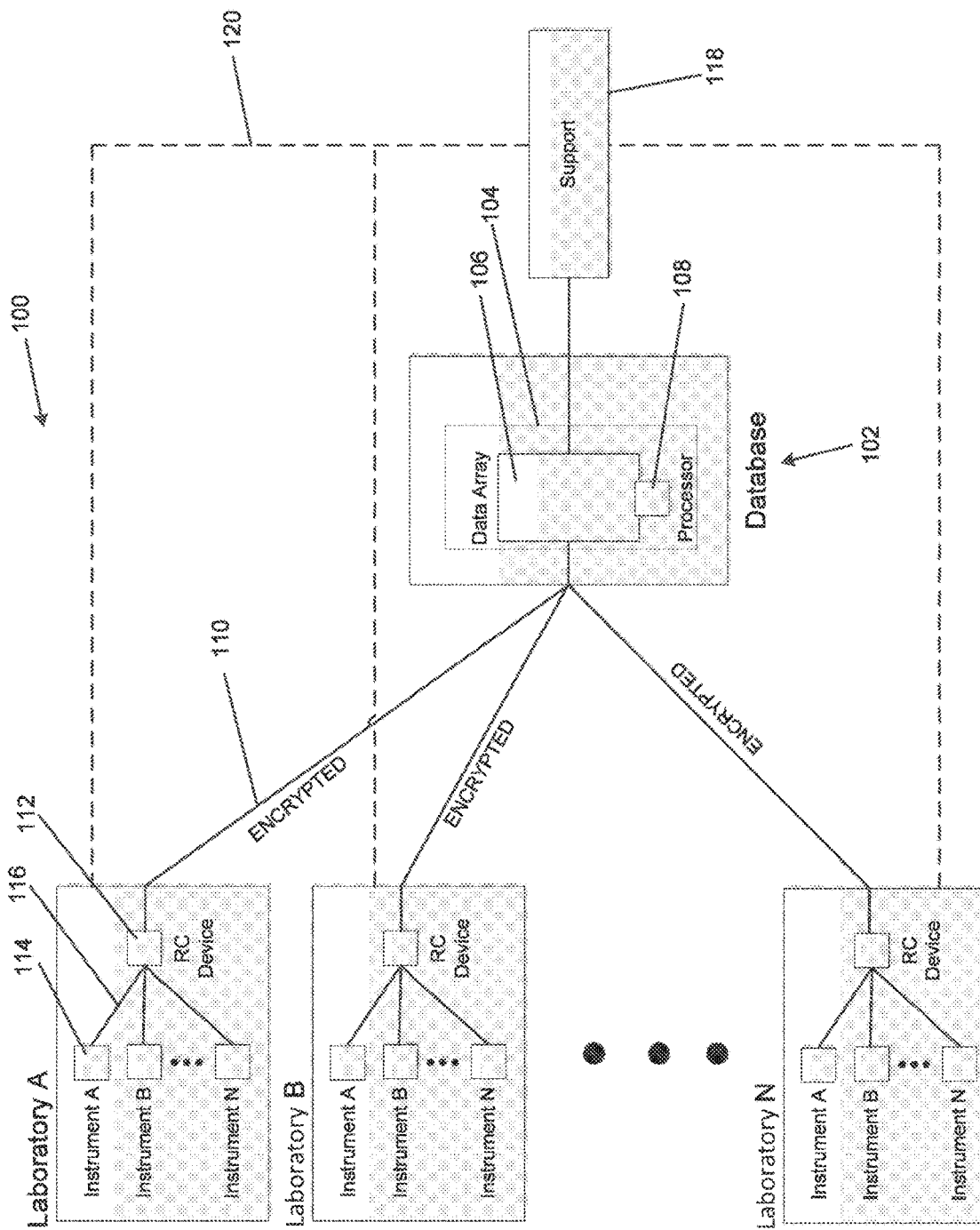
FIG. 1 is a high level schematic of an exemplary database system as described herein.

Described herein generally are database systems that may process data using at least one server and allow execution of a plurality of applications that may streamline the use and/or improve efficiency of analytical instruments at remote locations. In some embodiments, if described from an analytical instrument's point of view, the at least one server can be considered remote to the analytical system. In other words, the instrument(s) and the server(s) need not be in the same location, they may be remote or distributed relative to one another.

Some embodiments may include database systems that may transmit data from one or more instruments to one or more servers that may be configured to compile a database including rich data from instruments. In some other embodiment, servers may be configured to analyze rich data using an analytics program or a module that may be configured to perform analytics on data (hereinafter referred to as a module) and to display real-time or near real-time result of the analysis. In one embodiment, the module may be hardware. In another embodiment the module may be a software. In another embodiment the module may be a firmware. In another embodiment the module may be a combination of hardware and software. In some other embodiments, "rich data" may be understood as data which may be associated with metadata that allows it to be correlated with other data when neither the rich data nor the other data with which it would be correlated directly refers to or explicitly incorporates the other. In an example embodiment of "rich data", a measurement stored in a database with metadata indicating a serial number of an instrument, which took a measurement that would allow the measurement to be compared against measurements taken by other instruments purchased by the same customer using a customer database that correlated instrument serial numbers with customers.

In some embodiments, database systems described herein may be configured to execute a data analytics program or a module on one or more remote server(s) using at least one processor, that when applied to large amounts of rich data may provide solutions to stochastic phenomena that may otherwise not be evident from analyzing data from a single instrument.

In some other embodiments, rich data may be processed by at least one processor associated with one or more servers. In some other embodiments, processing of rich data may be by execution of a data analytics program or a module executed on the one or more servers by the one or more processors. In one embodiment, one or more processors associated with one or more servers may be configured to execute a data analytics program or module in a database. In some embodiments, the data analytics program or module may identify a stochastic phenomenon and suggest or even implement one or more remedies.

In some other embodiment, one or more processors associated with one or more servers may be configured to execute a program in a database to process data and present comparison information about one or more instruments at a location of the one or more instruments in real-time. In some other embodiments, such comparison data may be used to balance instrument workflow and/or staff workflow. In some embodiments, one or more processors may execute programs to automatically shift workflow to different instruments or cue workflow to transfer to different physical locations.

In some other embodiments, comparison data may be used to monitor consumables on one or more instruments, or in other words provide metering data. In some other embodiments, metering data may be analyzed and displayed over a period of time. In some other embodiment, metering data may be a reagent usage over time. In some other embodiment, metering data may be assay count over time.

In some embodiments, one or more processors may be configured to monitor reagent levels, for example, based on comparison and workflow analysis and automatically order or set a reminder to order reagents ahead of time to reduce instrument downtime. In some other embodiments, the processors may even shift workflow during reagent changes and system re-calibrations.

In some embodiments, transmission of rich data from one or more instruments to the one or more servers may be encrypted. In one embodiment, the encryption is at least 128-bit or 256-bit encryption. In other embodiments, one or more servers may be further configured to transmit data back to one or more instruments, and this data may also be encrypted with encryption similar to that used to transmit data to the server(s).

In some embodiments, any presentation of data or analysis of data may be in real-time or may be in near real-time. In some other embodiments, real time display of data may be on a device such as a computer workstation, display on an instrument, or a portable electronic device such as a mobile computer, mobile phone, PDA, laptop computer, tablet or similar device, and a user can make appropriate instrument changes on that device.

In some embodiments, a database system may provide system monitoring on instruments in the field. In some additional embodiments, database systems may include expanded data analysis and identification capabilities that may facilitate large-scale, complex investigations. In some other embodiments, several programs working in conjunction may enable efficient, large scale data analysis and management to ensure the proactive identification of factors that may contribute to system down time.

In some embodiments, a database system as described may be configured to collect data, for example rich data (in cases where instruments themselves are configured to communicate data in a form which may associate it with metadata) or a big-data data set (which should be understood as a large data set which may combine information gathered from multiple sources), from remotely located instruments and process the data for use with applications. In some other embodiments, a database system may include hardware such as a headless (e.g., not requiring a local display), small form factor computer that may be installed in a remote location and connected to a remote location network and the instruments. In some other embodiments, a Remote Communication processor (RC device or box) and software may enable transfer of data collected from a remotely located instrument to a server and processing of that data by at least one processor. In some example embodiments, the RC device may provide security for connected instruments, communication with a server and VPN tunneling for desktop sharing. In some embodiments, collected data may often be processed and used in various ways with the aid of applications to better serve instrument users, particularly through use of a user interface. In one embodiment, information in the form of data may be used to monitor the health of an instrument and alert service personnel to proactively respond to potential instrument issues, many times before they arise and result in unscheduled instrument outages and/or inaccurate results that may cost time and money. In other embodiments, data may be used to monitor multiple instruments in order to identify and/or rectify systematic instrument problems. In still other embodiments, data may be used to increase efficiency, monitor and enhance quality control, monitor and/or meter consumable usage, analyze behavioral patterns and/or patterns in sample types, and the like.

In some embodiments, any data described herein m be accessed in real-time or near real-time. In some other embodiments, "Real-time" as used herein may generally refer to updating of information at essentially a same rate as the data is received or processed. In yet some other embodiments, "real-time" may be intended to mean that data is acquired, processed, and transmitted from the instrument through the RC device and processed by the database at a sufficiently high data rate and at a sufficiently low time delay that when the data is displayed, it may be displayed smoothly without user-noticeable judder, latency or lag. In some other embodiments, near real-time on the other hand may be where information is updated at substantially the same rate as the data is received or processed, but with minimal lag time.

In some embodiments, there may be provided a computer program product comprising a non-transitory computer readable medium encoded with instructions for a processor to perform a set of acts. Such a set of acts may comprise receiving rich data from one or more remote analytical instruments, compiling a repository of the rich data, and identifying a stochastic phenomenon associated with the one or more remote analytical instruments using both real time and historical data previously compiled in the repository.

In some embodiments, a set of acts for performance by a processor based on instructions encoded on a non-transitory computer readable medium may comprise determining one or more solutions to a stochastic phenomenon in real time, ranking the one or more solutions in ascending order, providing a ranked list of the one or more solutions to the one or more instructions at the location of the one or more instruments in real time, and applying corrective measures to the one or more instruments in real time. In some embodiments at least one solution may be provided in real time on a portable devices, which may be a portable electronic device. In some embodiments, the at least one solution may comprise comparison information of the one or more instruments. In some embodiments, such comparison information may comprise meta data associated with the one or more instruments, which may include at least one of: reagent usage data, calibration data, assay count data, and instrument serial number data.

In some embodiments, a set of acts for performance by a processor based on instructions encoded on a non-transitory computer readable medium may comprise identifying a stochastic phenomenon by executing a data analytics module. Additionally, in some embodiments where a computer program product is provided which is encoded with instructions for performing a set of acts comprising receiving rich data from one or more remote analytical instruments, that act may comprise receiving the rich data in encrypted form. Additionally, in such an embodiment, the set of acts may also comprise transmitting data to the one or more remote analytical instruments in encrypted form.

Database systems as described herein can include various components that allow data streamlining, analysis, and presentation to occur. One non-limiting exemplary system is illustrated in FIG. 1. Data analytic network or database system 100 includes a database 102 that includes at least one server 104 that is used to collect and analyze data stored in one or more data arrays 106. The server is controlled and data is processed and/or analyzed by one or more processors 108 that are associated with server 104 and interact with data arrays 106. The one or more processors 108 can include one or more processors communicatively coupled by an address/data bus to one or more data arrays 106, other computer circuitry, and one or more interfaces as will be described herein. Data array 106 can be housed on any appropriate storage medium.

The database 102 can be connected through the internet and one or more encrypted connections 110 such as a remote data collection pipeline to a RC device 112 at each laboratory location. Each laboratory can have an analytical instrument 114 that is connected to RC device 112 through a local link 116. Each laboratory can have up to N instruments. N can be virtually any number of instruments, for example, 5, 10, 20, 50, 100, 1,000 or more. These instruments can form a local network with RC device 112 connected to the database 102.

In some embodiments, the processor may be any suitable processor, such as a microprocessor from the Intel PENTIUM®, CORE™, or XEON®; Advanced Micro Devices (AMD) FX, A, ATHLON®, or OPTERON®; Broadcom, NVidia, Qualcomm, IBM, Marvell, Sun, Cyrix, Via, Freescale, or Texas Instruments' family of microprocessors. In some embodiments, data array 106 may store a software program that interacts with other devices in database system 100, as described. In some other embodiments, software programs may be executed by one or more processors 108 in any suitable manner. In an example embodiment, data array 106 may be part of a "cloud" such that cloud computing may be utilized.

In some embodiments. database server 102 may include any kind of data including databases, programs, applications, files, libraries, records, images, documents, instrument manuals, instrument automation data, instrument operational data, instrument health data, configuration data, warranty data, service contract data, index or tagging data, purchase information, statistical data, reagent data, flow cell data, detector data, source data, sample data, date stamped data, etc. In some other embodiments, a server may store and operate various applications as described herein in order to streamline instrument function. It should be appreciated that various configurations of one or more servers may be used to support and maintain server 102. In an example embodiment, many different servers may be operated by various different entities. In some other embodiments, certain data may be stored in certain servers within a database system that can act as server 102.

In some embodiments, at least one server 104 may host database applications such as Oracle, Hadoop, or the like. In some other embodiments, the database application may store and process sufficient instrument data to provide an interface with real-time analytics or real-time updates of processed data. In some other embodiments, the database application may be able to store and process, using at least one processor, sufficient instrument data to provide an interface with real-time analytics or real-time updates of processed data.

In some embodiments, data array 106 may be implemented by any computer-readable medium, including random access memory (RAM), read-only memory (ROM), flash memory, magnetic or optical disks, optical memory, solid state memory, or other storage media. In some other embodiments, an array may be housed on a redundant array such as a redundant array of independent disks (RAID) array or other type of redundant array to protect the data being stored and/or analyzed. In some other embodiments, data array 106 may include sufficient space to store data from the remote instruments. In some other embodiments, sufficient space may be at least about 1 terabyte, at least about 1 pentabyte, at least about 1 exabyte, at least about 1 zetabyte, or more.

In some embodiments, interface between database server 102, RC device 112 and instruments 114 may be implemented using any suitable interface standard, such as fast Ethernet connection, gigabit Ethernet, universal serial bus (USB), digital subscriber line (DSL), telephone line, coaxial cable, fiber optic cable, wireless connections, and the like.

In some embodiments, one or more input devices may be connected to database server 102, RC device 112 and instruments 114 for entering data and commands into a respective device. In an example embodiment, an input device may be a keyboard, mouse, touch screen, track pad, track ball, isopoint, image sensor, character recognition, barcode scanner, microphone, and/or a speech or voice recognition system, or the like.

In some embodiments, one or more displays, printers, speakers, and/or other output devices may also be connected to database server 102, RC device 112 and instruments 114. In some embodiments, the display may be a cathode ray tube (CRTs), a liquid crystal display (LCD), or any other type of display. In some other embodiments, each display may generate application interfaces or dashboards as described herein. In some embodiments, an application interface or dashboard may include prompts for human input from a user including links, buttons, tabs, checkboxes, thumbnails, text fields, drop down boxes, etc., and may provide various outputs in response to the user inputs, such as text, still images, videos, audio, and animations.

In some embodiments, a database as described herein may not actually be in the physical possession of the service provider. In some other embodiments, a database may be cloud based meaning that it may reside on cloud based servers at unspecified locations. In some other embodiments, even with a cloud based database, encryption described herein may still be used. In some embodiments, encryption may be used to provide privacy wherein protocols may used to protect personal information and/or data. Likewise, in yet some other embodiments, encryption may be used to provide security wherein protocols are used to protect the integrity of the system. In some embodiments, both privacy and security may be provided by encryption described herein. In other embodiments, privacy or security may be implemented.

In some embodiments, each encrypted connection 110 may have security built in to prevent intrusion by third parties. In some other embodiments, encryption may be any standard 64-bit, 128-bit, 256-bit, 512-bit, 1,024-bit, 2,048-bit or more encryption. In some other embodiments, encrypted connection may be SSL protected and/or be routed via a VPN link.

In some embodiments, RC device 112 may serve as a firewall to prevent local network traffic from compromising the encrypted link to database 102. In some other embodiments, as instruments are connected directly to RC device 112, RC device 112 may prevent local network users from accessing the instruments.

In some embodiments, a RC device may not be needed to connect instruments to a database. In these embodiments, a firewall hardware or software may be built into the instruments themselves and provides an encrypted connection, e.g., VPN, to the database. In some embodiments, even an encrypted data connection may not be needed. In some embodiments, a database may be included at the location of the instruments that can analyze local instrument trends and even report the local data to a remote database, such as database 102 for further processing and analysis on a region wide instrument network.

In some embodiments, a region wide instrument network can include instruments in a company, city or municipality, state, region, hemisphere, country, on a continent, worldwide or the like.

Virtually any number of laboratories may have an encrypted connection 110 to database 102. In one embodiment, N laboratories may be connected to database 102. N may be virtually any number, for example, 5, 10, 20, 50, 100, 1,000, 10,000, 100,000, 1,000,000, or more.

In some embodiments, instruments from different manufacturers may be used with the presently described database systems and associated applications. In one embodiment, the RC device and/or the database 102 may interface and collect data from instruments from virtually any manufacturer. Again, in some embodiments, a RC device is not required in order for the instruments to communicate with a database.

Instrument 114 may be any serviceable instrument. In some embodiments, instruments may be analytical and/or diagnostic instruments and/or systems. In other embodiments, instruments may include chemistry, immunoassay, hematology, flow cytometry, chromatography, mass spectrometry, nuclear magnetic resonance spectroscopy, fluoroscopy, clinical automation and middleware instruments and/or systems. In still other embodiments, instruments may be any device that can have a consumable part or substance that needs replacement.

In some embodiments, systems such as described herein may be used in environments where turnaround time is critical. For example, physicians frequently require prompt and accurate results and an inoperable system may directly impact the laboratory's ability to deliver results to physicians. Thus, in some embodiments the systems and methods described herein may provide solutions that may efficiently analyze and diagnose, in real-time or near real time, large amounts of system data for root cause analysis and help to prevent unscheduled instrument outages and/or inaccurate results that can cost time and money.

In some embodiments, support 118 may be the manufacturer of the instruments, a service provider, a contractor for service, a tech support division, or the like. In various embodiments, support 118 may provide either remote diagnostic to the instruments through an encrypted connection 110 or may send field agents to the instruments along in-field service 120.

In some embodiments, when instrument issues are identified that cannot be resolved remotely, the database system may help streamline the service process. Precise problem diagnosis may allow necessary repairs to be planned for and any necessary parts to be allocated and brought along. This may help ensure that the issue can be resolved the first time with minimal interruptions to potentially time-sensitive workflow.

In some embodiments, the database systems described herein may allow an instrument user to utilize the encrypted internet connection to access the service provider's support resources directly through the instrument console. This may allow a user to access product information, support services and lab management utilities, such as quality assurance programs, in real time. The connection may also enable metered billing and reagent auto replenishment, where available.

Figure 27:
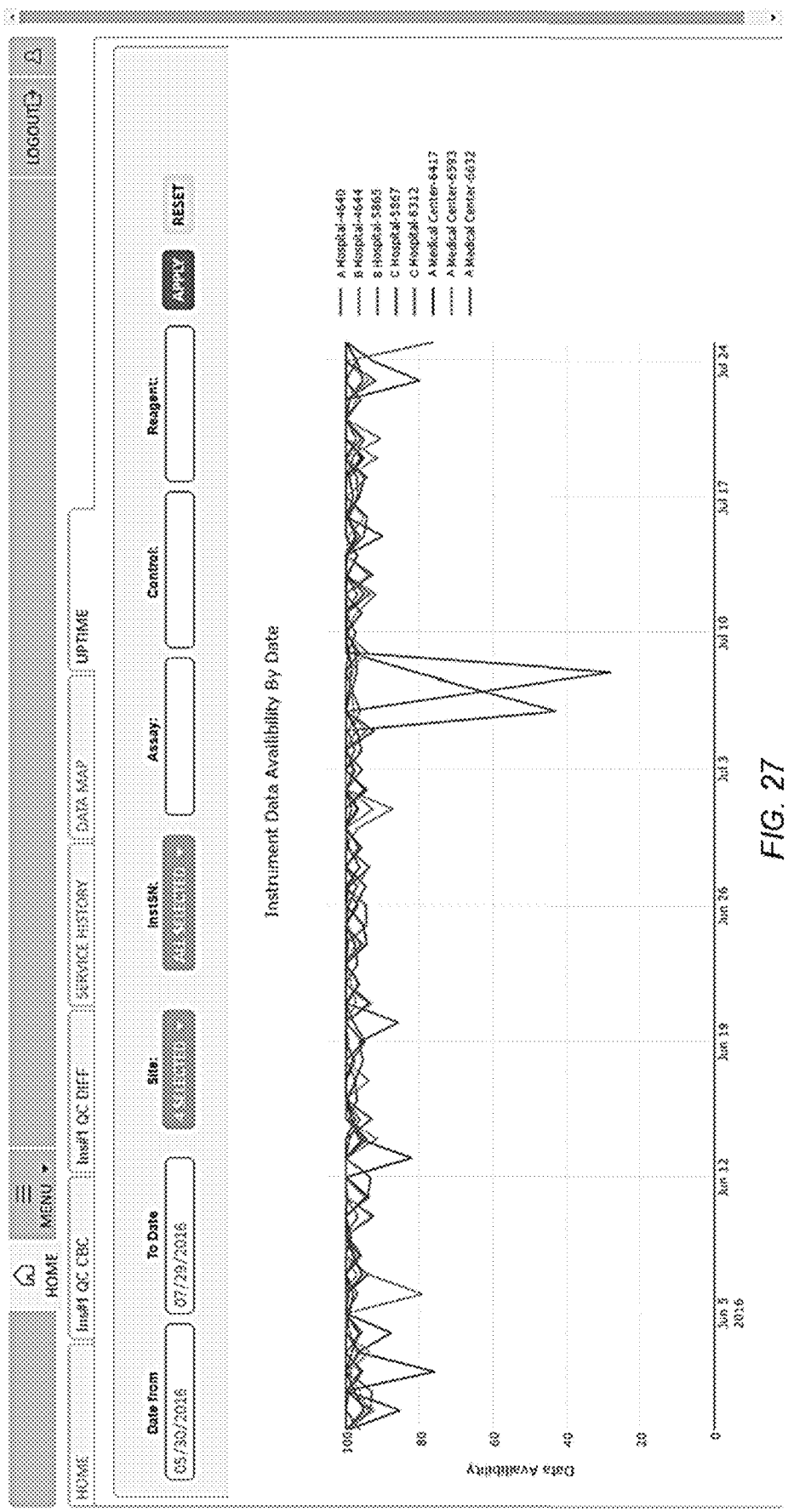
FIG. 27 is an exemplary interface which can provide uptime and/or data availability information for instruments at various sites.
Figure 28:
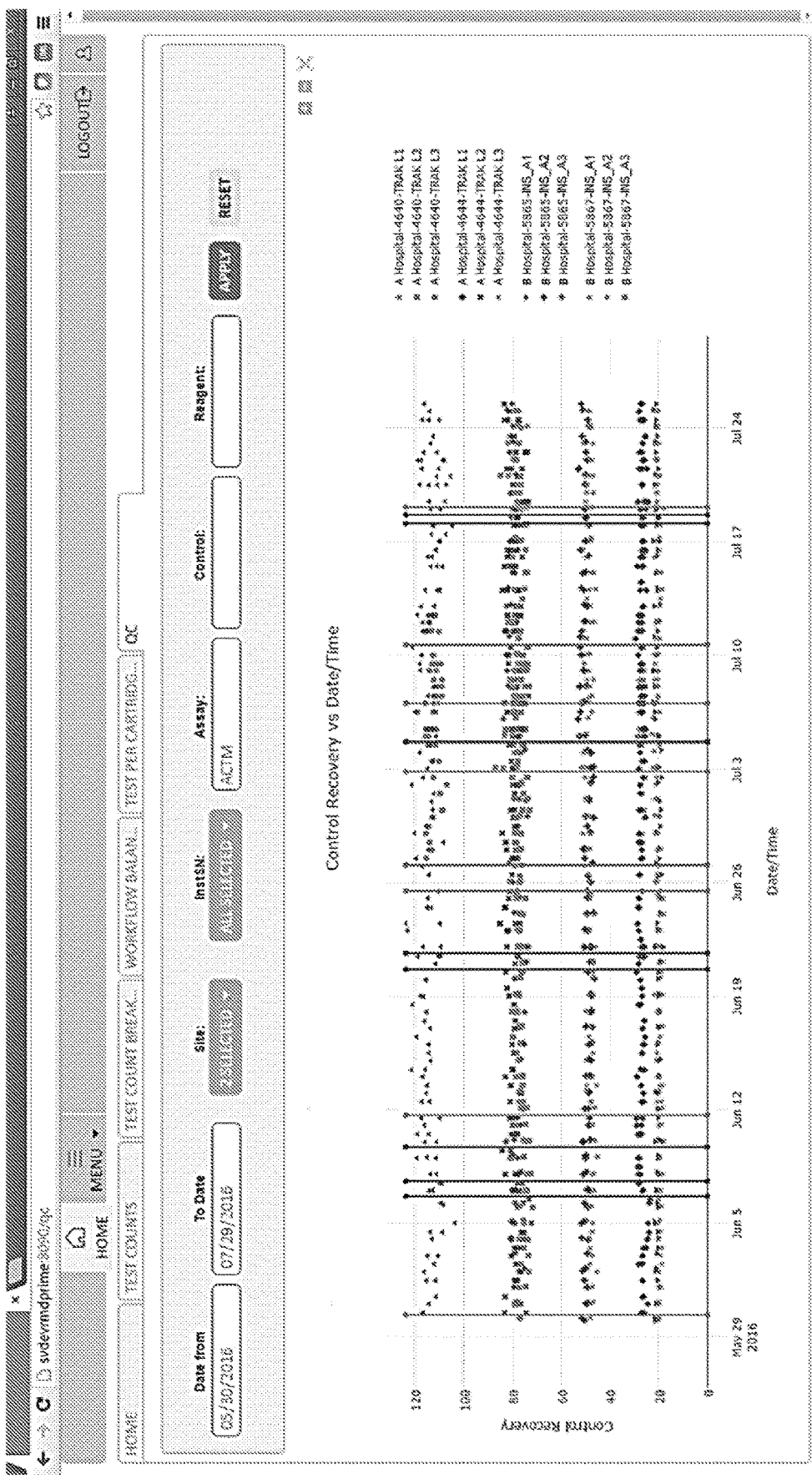
FIG. 28 is an exemplary interface which presents cross site comparisons of control recovery of various instruments.
Figure 30:
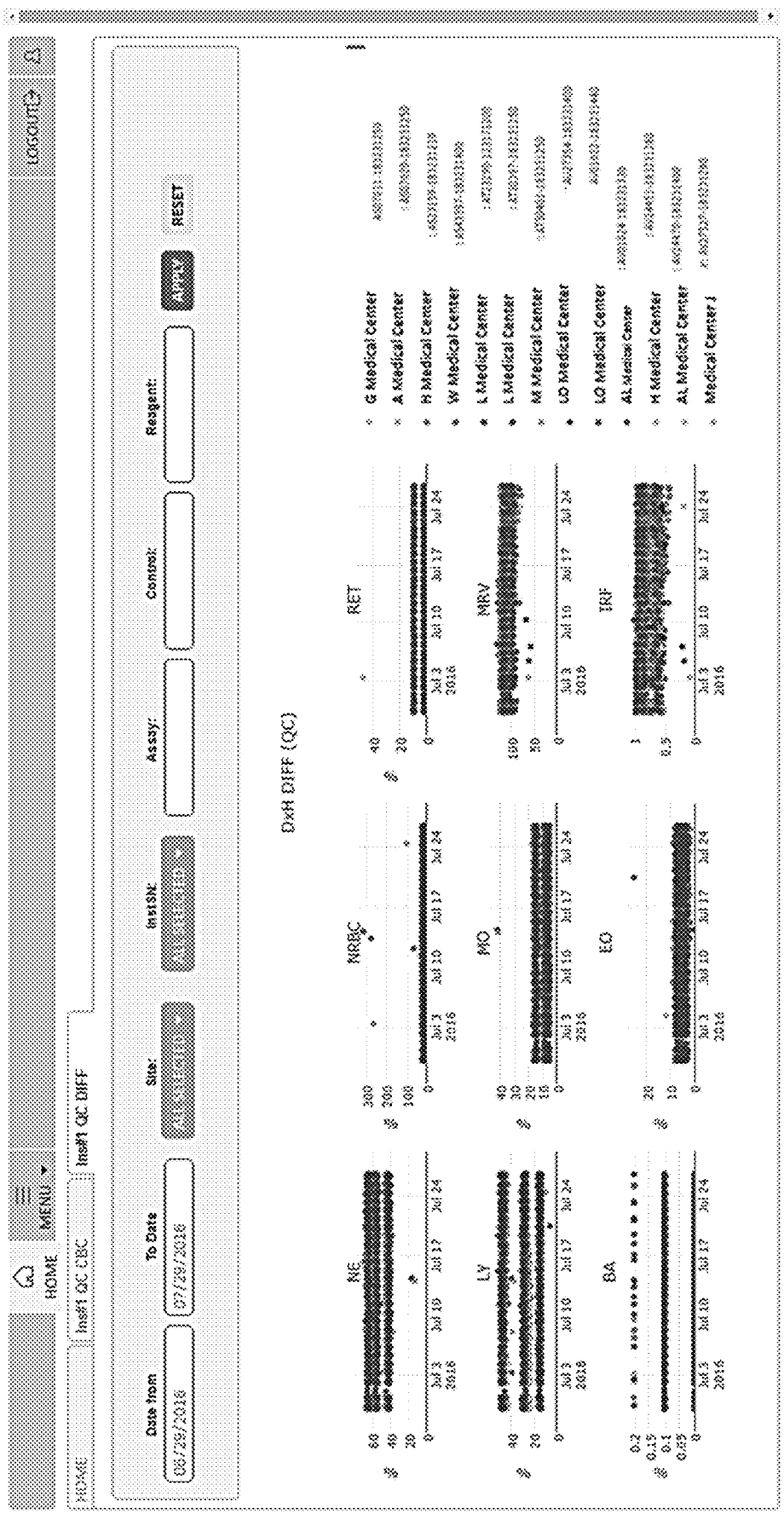
FIG. 30 is an exemplary interface of a peer comparison of QC control charts of different blood differential.

The database systems described herein may include remote management and diagnostics systems through the encrypted connection to facilitate continuous transfer and analysis of system performance data from the instruments to the servers to diagnose current and potential future problems. This type of continuous transfer may be monitored by individuals who are responsible for the instruments, such as using an uptime/data availability interface such as shown in FIG. 27, which may be presented as part of an application as described infra. Further, in some embodiments the servers may analyze data pooled from multiple instruments in many different geographic locations to diagnose current and potential future problems based on data trends identified by the at least one processor or a user visualizing the data on an application interface.

In some embodiments, a diverse set of safeguards may be built into the database systems described herein to protect connected instruments and the data they transmit, and control who has access to the system. In some embodiments, data transmitted to the servers may pertain to instrument function and may be used by the service provider to help identify, diagnose, troubleshoot and resolve system issues. In other words, specific data relating to confidential patient data generated on the affected instruments is not comprised. For example, desktop sharing sessions may require authorization from the location where the instrument is located from an authorized individual.

In some embodiments, the framework of systems such as described herein may be designed for monitoring of analytical instrument functions through a diagnostic server dashboard which may provide system information on an instrument-by-instrument basis in real-time. The systems and methods may allow service and support personnel to access, in near real-time, system status, and may track user-defined system parameters to trigger performance warnings.

In some embodiments, the systems may include a big-data server, such as a Hadoop server. Such a server may enable the storing and processing of big-data data sets in a distributed fashion on large clusters of commodity hardware. Essentially, the big-data server may provide large-scale, multi-dimensional data analysis of data stored on one or more diagnostic servers over time. Data incoming from remote analytical instruments may be channeled through applications run by the present systems and/or on the diagnostic servers and the output may be used in the form of various applications viewed through an interface by technical support and product development engineers to proactively track, monitor, diagnose and resolve issues with remote analytical systems.

In some embodiments, a database system including a remote monitoring and diagnostic system may use information collected from instruments to provide instrument and engineering support through applications to a service provider. There may be numerous applications that rely on information collected from remote instruments to provide value-added services to users. A few of these examples include inter-laboratory quality assurance programs, metering, and product development.

Figure 2A:
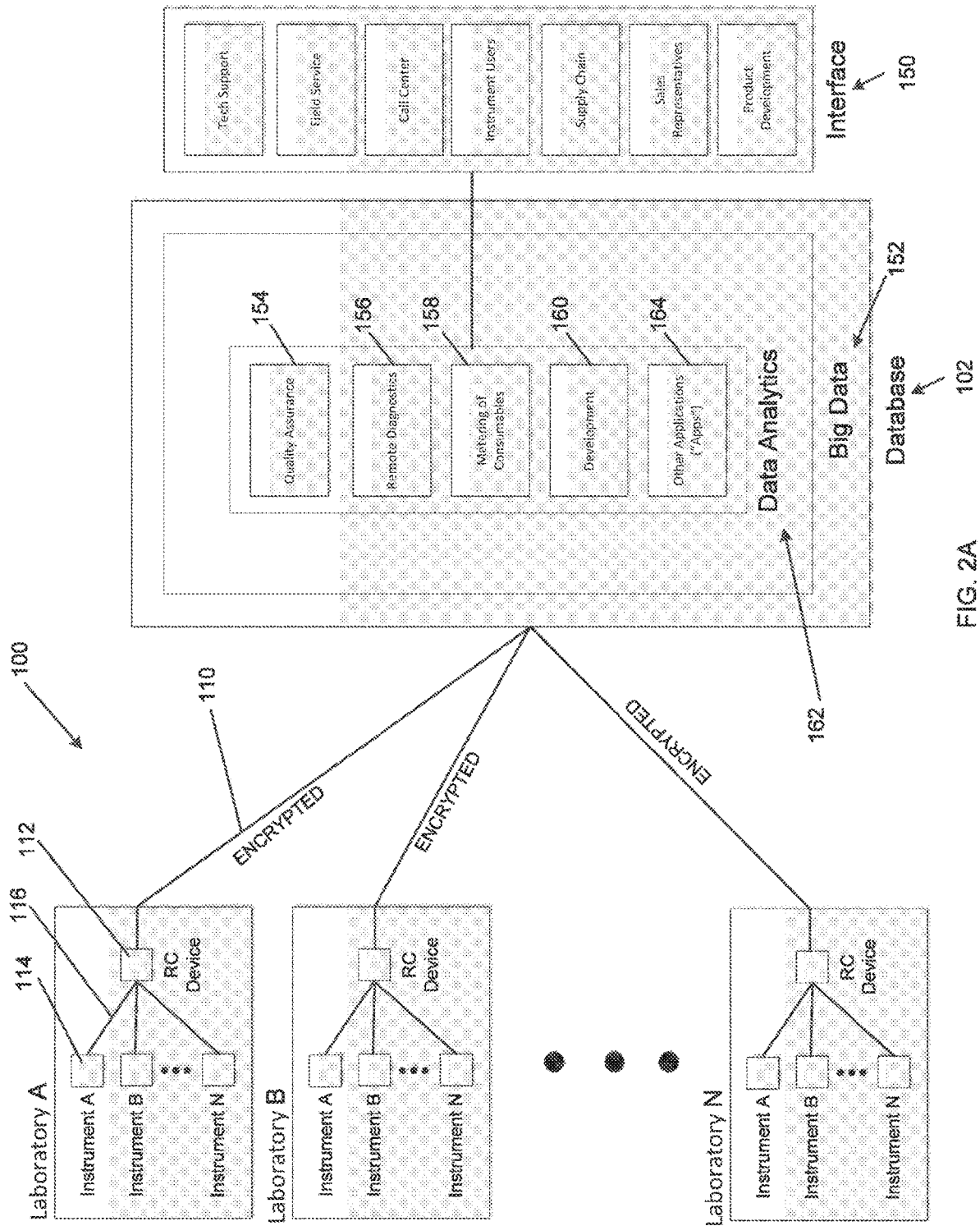
FIG. 2A is another high level schematic of an exemplary database system as described herein.

In one embodiment of a database system 100 illustrated in FIG. 2A, the system includes an interface 150. Interface 150 may be a web based or application interface or dashboard. Interface 150 may be useful and/or used for/by tech support, field service personnel, call centers, instrument users, and/or laboratories to retrieve instrument information and order parts and consumables. Interface 150 may also be useful and/or used for/by supply chain parties, sales representatives, and product developers.

In some embodiments, interface 150 may be fed information from applications run in the database 102. Interface may run on an instrument, on a remote computer, or on the server itself. If not run on the server, applications may access data on the server that has been processed by the server and further process the data on the device and display it on an interface on the device itself. In one embodiment, as previously discussed, database 102 may host a big-data, rich database application 152 such as a Hadoop server database. The database application 102 may host rich data that includes raw data stamped with a time, date, unit of measure, level of severity, and the like.

In some embodiments, the processor in the server may analyze data in big-data, rich database application 152, to provide trends in the data. This analyzing is referred to as data analytics 162. Data analytics 162 may use rich data collected from remote instruments to provide more insight on how the instrument and instrument consumables are used. Data analytics 162 may perform analytics (through various tools/numerical models/business intelligence) on rich data remotely collected from instruments across different labs. As a result, in some embodiments an instrument user may be able to build various graphs or reports (such as instrument status, test volume, reagent usage, etc.) based on the collected data. Further, in some embodiments business intelligence may also be built for predictive modeling of instrument failure/maintenance and inventory management.

In some embodiments, data analytics 162 may supply transformed data or data that has been analyzed for trends through the use of the at least one processor 108. This analyzed/transformed data may be fed into a suite of applications developed to be fed from the data analytics program or the module. In some embodiments, the module may be hardware and/or software and/or a combination of thereof. In various embodiments, the applications may be hosted from the database directly or may be hosted on remote devices that can access the data remotely and securely and display it in a local interface or dashboard.

Figure 2B:
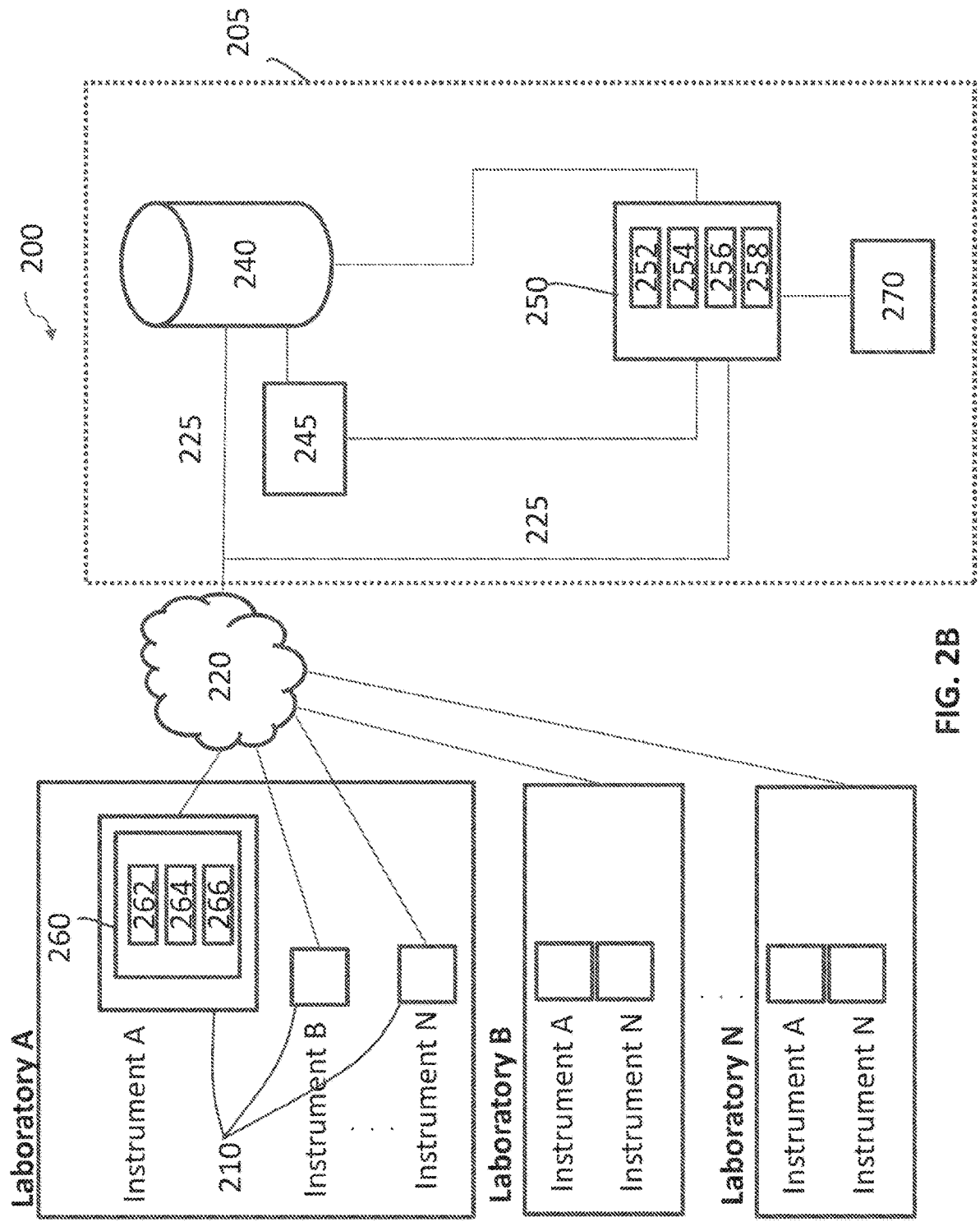
FIG. 2B is yet another high level schematic of an exemplary database system as described herein.

FIG. 2B illustrates another exemplary embodiment of a database system, database system 200. Database system 200 provides an avenue for various applications to be customized and built by laboratory users or instrument service providers. The term "application" as used herein and the entire document may refer to applications, application modules, report generators, data-mining reports, services, service modules, and the like, which can be hosted by the cloud 220 or built by application builder 250 for use by an end user. In other embodiments, applications may be hosted by database 102 as described herein.

As with the systems illustrated in FIG. 1 and FIG. 2A, in some embodiments N laboratories may be connected to content provider 205 and/or cloud operating environment 220. N may be virtually any number, for example, 5, 10, 20, 50, 100, 1,000, 10,000, 100,000, 1,000,000, or more. Further, each laboratory can have up to N instruments. N can be virtually any number of instruments, for example, 5, 10, 20, 50, 100, 1,000 or more.

In some embodiments, database system 200 may include instruments 210, a cloud operating environment 220, and a content provider 205 that enables the collection of data from instruments 210 for building applications for inventory, instrument, and laboratory management, and instrument and patient data diagnosis applications, for example. Content provider 205 may include a remote data collection pipeline 225, an external data module 245, a data store 240, and an application builder 250. In some embodiments, instruments 210, cloud 220, and content provider 205 may belong to three different companies or entities, respectively. However, the provided instrument architecture, computer network, security, and common interface between instruments 210, cloud 220, and content provider 205 may enable the components to operate as one large operating framework so data collection and exchange are possible.

In some embodiments, instruments 210 may communicate with cloud 220 through any numbers of networks through a security, e.g., encrypted, firewall as mentioned herein. In some embodiments, instruments 210 are similar to instruments 114 of FIGS. 1 and 2A. In one embodiment, each instrument 210 may include a rich data generation module 260 that provides rich data, e.g., data with traceability. That is, rich data generation module 260 may provide details to all collected data so that there is enough information to characterize, interpret and correlate the collected data to provide ongoing instrument support, assay support, and data mining. In some embodiments, for every result or data generated by in instrument 210, rich data generation module 260 provides one or more of the following associated tag information: lot and serial number information for calibrators, controls and reagents information, calibration results, control results, raw data, assay parameters used to generate results, sample type, description and container type, sample quality indices generated by instrument users, the underlying raw result data, non-HIPAA sample specific information which might affect a test result, actual patient sample in hospital, maintenance and service records, and other relevant system information.

In some embodiments, rich data generation module 260 may include a tag ID file generator 262 that provides index and label to each data, and a log file generator 264 that provides a tag header with information mentioned above and time stamps to all collected data. In some embodiments, module 260 may further include a patient data masking module 266 that replaces all personal information associated with a test sample with a generic ID that is in compliance with HIPAA requirements.

In some embodiments, cloud 220 may include a cloud services operating system and other operating systems and platforms. In some embodiments, cloud 220 may include services such as computing, storage and content delivery, databases and networking. These services may be operating under a third-party vendor's administration controls, which include identity management, auditing, encryption key creation and management, monitoring and logging, or under the owner of the content provider 205. In some embodiments, cloud 220 may further include tools for analytics that may be used by an end user or a development environment that developers may use to build applications.

In some embodiments, rich data may be collected via remote data collection pipeline 225 which can be similar to secured, encrypted connection 110. Pipeline 225 may provide a secure IP network connection linking a remotely located instrument(s), e.g., instruments 210, within a clinical laboratory to data store 240 for the purposes of gathering rich data—that is, instrument data, test data (test results of a hematology test analysis for example), reagent usage data, quality control data, and troubleshooting information with tags, to provide remote management of instruments and data analysis. In some embodiments, pipeline 225 may include hardware and software having program modules, operating environments, software code and the like for acquiring data from the cloud 220 and storing the acquired data on a storage media in data store 240. In one embodiment, data store 240 may include a database or other data storage modules. Data store 240 may reside on a single device, or may be distributed across several devices such as, for instance, a Hadoop server. In some embodiments, data store 240 may be configured to be searchable, for instance, it may include a table or relational table of rich data to facilitate data-mining and application building.

In one embodiment, content provider 205 may further include an external data module 245. External data module 245 may include data gathered from historical data, or data provided by external organizations such as hospitals, universities, public health organizations, or research organizations relating to patient health, disease conditions and states, clinical laboratory data for decision support, and the like. Together, data from the external data module 245 and data store 240 may provide even richer information and intelligence to the data collected. For example, data from external module 245 may contain patient information such as treatment plans, prescription drugs, implanted medical devices, invasive and non-invasive procedures, diseases and parameters, and the like that are often associated with certain test results obtained from instruments 210. In some embodiments, external data module 245 may be connected to data store 240 such that the external data is incorporated with rich data to provide data with even richer information and intelligence. Alternatively, in some embodiments, external data module 245 may be a standalone module that is connected to application builder 250 and may be called upon or invoked only as needed. While the external data module 245 is represented as one data source in FIG. 2B, it may be comprised of different modules or databases from different entities, such as those mentioned above.

As illustrated in FIG. 2B, database system 200 includes an application builder 250. The application builder 250 includes several modules that enable different types of users to get access to rich data for developing their respective applications. Application builder 250 includes an identification (ID) module 252, a security module 254, an analysis module 256, and a reporting module 258. Application builder 250 can also include other modules and is not limited to the aforementioned modules.

Identification module 252 can create a user ID associated with a user of the application builder 250. The user ID can be associated with different security clearance for a technical support representative, field-service personnel, a call center representative, a sales representative, an instrument user, a product development user, or inventory management/supply chain personnel. Alternatively, the user ID can be categorized as an external or internal user for different access right to rich data. An internal user with a high level of security clearance for instance, has access to all rich data at all sites, that is, all data from cloud 220, data store 240, and external data module 245, whereas an external user with a lower level of security clearance can only have limited access to certain sites or limited access to data at each site. As shown in FIG. 2B, application builder 250 can direct get access to rich data stored in cloud 220. Again, the type of rich data accessible to a user will be defined by the user ID. For instance, an external user such as a Laboratory A user can only get access to rich data across multiple instruments located within Laboratory A and not within Laboratory B or any other laboratory he/she does not have access to. An external user with a higher security clearance, such as an owner of both Laboratory A and Laboratory B will be able to access rich data from both labs. On the other hand, and internal user such as a product developer with an even higher level of security clearance would be able to get access to all data residing within the cloud 220, data store 240, and external data module 245.

Application builder 250 may also include a data privacy module 254. Module 254 is provided to protect patient privacy and at the same time allow relevant data to remain so data mining is possible. For example, relevant data may include demographics such as age, gender, and race. Relevant data may also include geographical location, birth places, jobs, interests, and the like. In certain embodiments, data privacy module 254 comprises a process of de-identification of patient names and social security or patient record numbers.

In various embodiments, a data-mining module 256 is provided. Data-mining module 256 retrieves rich data from data store 240, and/or external data module 245, and cloud 220 based on the parameters requested by the application builder 250 and based on the user ID. Data-mining module 256 allows a user to build data correlation, statistical analysis, data trends, frequency counts, time-series analysis, and the like on rich data, including high-dimensional heterogeneous data that have temporal correlations, missing values and asynchronous streams. In some embodiments, data-mining module 256 includes tools for developers to build models that can be used to predict instrument performance and failures, manage inventory, identify probable causes, discover trends and disease conditions, detect anomalous behavior for quality improvement, clinical benchmarking, and clinical decision support.

In one embodiment, data-mining module 256 is used to build inventory management. That is, data-mining module 256 pulls data from cloud 220 via data pipeline 225 that provides real-time or near real-time access to data storage within cloud 220 to get the most up-to-date data of consumable usage and levels on an instrument, such as reagents, test tubes and buffers. When a consumable reaches a threshold as provided by analysis of historical rich data in data store 240 or provided by the external data module 245, an inventory ticket is automatically generated and routed to a laboratory manager and/or a supplier for fulfillment. A threshold can be determined based on the amount of consumable needed to run tests on an instrument for a period of time. The period of time can be one month, three weeks, two weeks, or one week, for example.

In another embodiment, data-mining module 256 is used to predict disease conditions. For example, data-mining module 256 collects all blood test data relating to mean corpuscular volume (MCV) and average red blood cell volume from cloud 220 or data store 240 and compares them to a threshold number provided by external data module 245. When the test data exceeds a threshold, the test data is flagged for a disease condition, such as vitamin B12 deficiency and/or folate deficiency and an alert is sent back to the instrument and/or laboratory where the test was conducted or to a health care provider.

In another embodiment, the external data module 245 contains training materials of patients with a known disease condition such as cardiovascular disease and their associated test results such as blood chemistry test results, complete blood count (CBC), reticulocyte characteristics, and five part differential results of white blood cells. In this embodiment, the data-mining module 256 is a neural network that uses the data training set from the external data module 245 to train the neural network to recognize the disease condition. Test results relating to chemistry, CBC, reticulocyte characteristics, and five part differential results of white blood cells (parameters), for example of a patient sample provided from cloud 220 or data store 240, may be run against the neural network to determine the disease. If the parameters fit, the test result is flagged for the disease and an alert is sent back to the instrument and/or laboratory where the test was conducted and/or to a health care provider. In a further embodiment, when a disease such as cardiovascular disease is determined by the data-mining module 256, another application built by the data-mining module 256 would look up treatments and preventative measures conducted for patients with similar diseases in the external data module 245 and display the information to a user. The displayed information can be medication needed for treatment or a suggestion list of preventive measures such as the cutting down the intake of trans fats, losing weight, and quitting smoking, or any other measures that can aid the user to deal with a patient with risks of a heart attack.

Results generated by the data-mining module 256 can be presented via a reporting module 258. Reporting module 258 prepares all information processed by the data-mining module 256 and presents the information to the developer or end user on a display device 270 through a portal, for example connected to the application builder 250. Display device 270 may be a computer terminal, or a handheld device such as a smart phone, a tablet, and the like. The presented data may be in charts, graphs, tables, flow diagrams, instructions, and the like. Various graphical presentations are discussed herein in FIGS. 3-8 and 10-30.

In one embodiment, the database may host a quality assurance application 154 that may generate reports of, for example, instrument health.

In some embodiments where it is present, a quality assurance application 154 may allow a user to obtain peer group comparison reports to gauge his or her own laboratory's quality control (QC) data. For this type of functionality, quality control files or data from instruments may be collected at database 102. The data may then undergo statistical analysis and the results may be displayed at interface 150. The user may then log in and get statistical results. There are a few instances where the QC data from an instrument may be sent to quality assurance application 154: a user may go to a website and enter the data manually using a web form; a user may go to the website and upload the QC file that was generated by the instrument; a user may send the QC data directly from the instrument to database 102 via the RC device using the instrument software; or a user may mail out a media file containing the QC data to be loaded locally into database 102.

Figure 3:
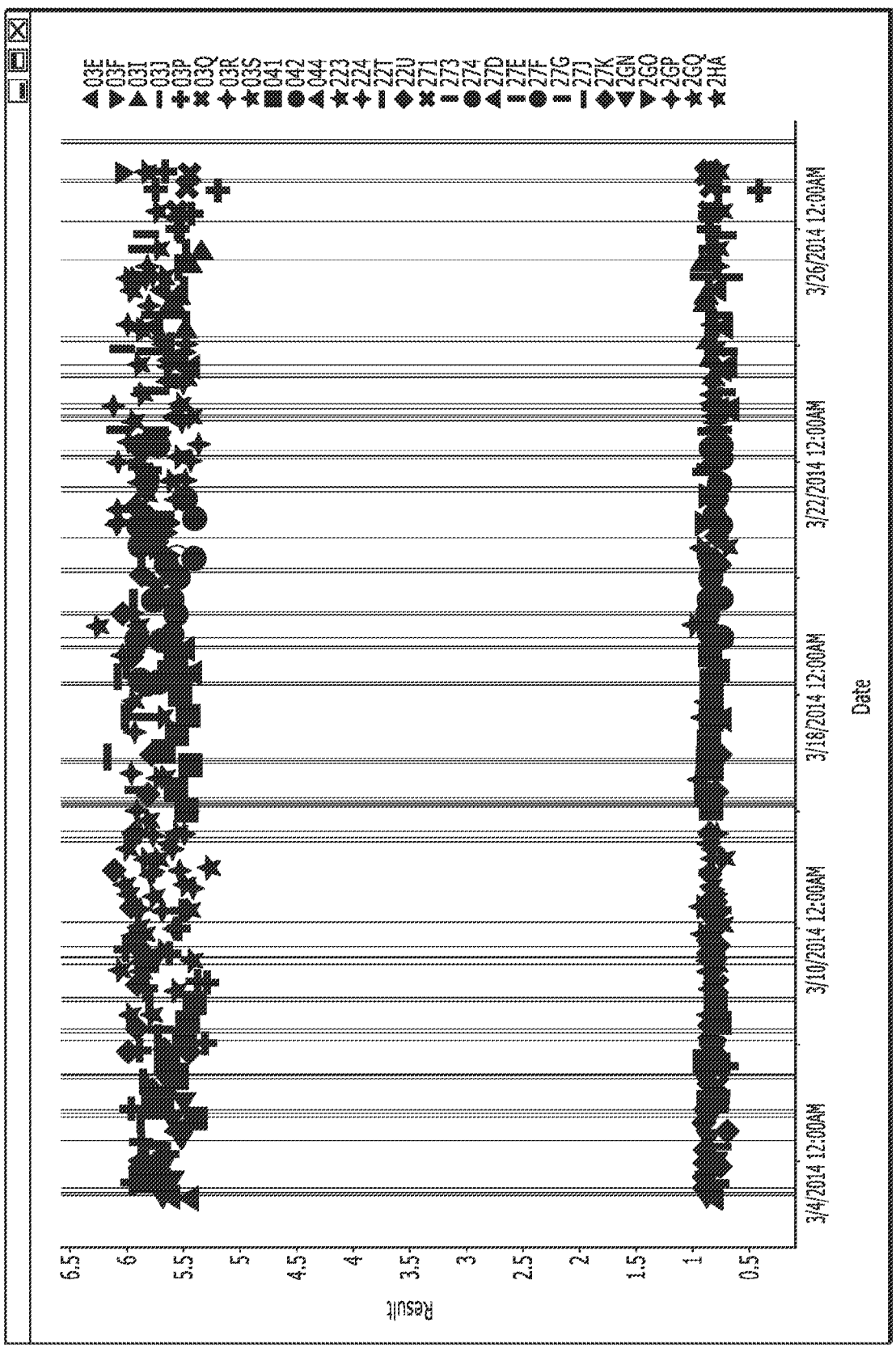
Figure 24:
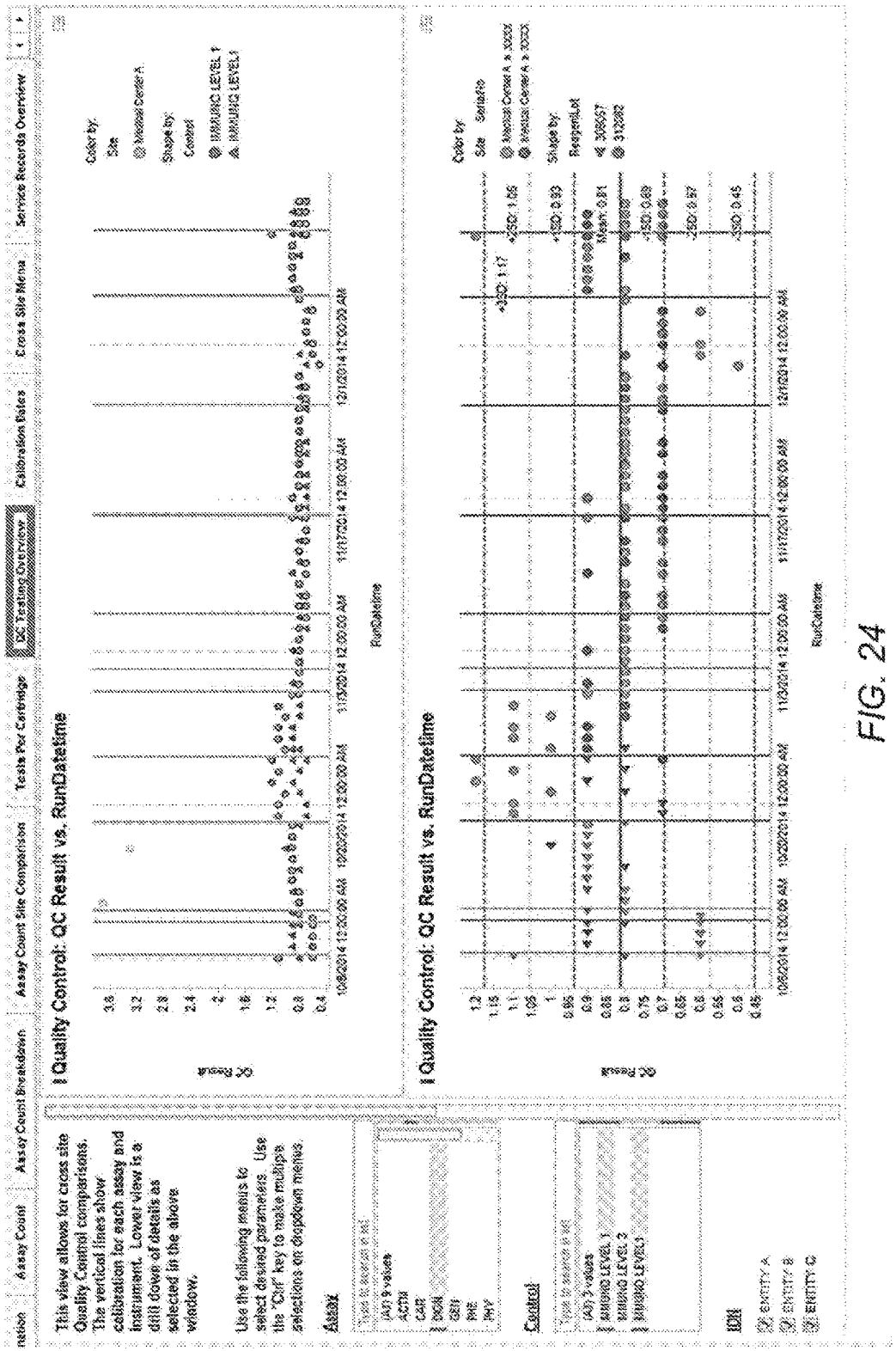
FIG. 24 is an exemplary interface which presents quality control test data.

FIG. 3 illustrates a report which could be generated by an application built using the application builder 250 for example. The report is a calibration graph organized by reagent lot number and serial number over time. Different shapes indicate reagent serial numbers within a reagent lot. In some embodiments, different colors (not illustrated in FIG. 3) or color/grayscale intensity may be used to indicate different reagent lots. For a quality control standpoint, instrument calibration over time may be visualized. Similar interfaces may also be used for other types of quality control data. For example, FIG. 24 presents an interface which may present the results of quality control tests which are performed at particular sites.

Outliers may be investigated. For example, a low calibration line has an outlier that falls below the line. The database system processor may analyze the big-data data set using data analytics to determine potential root causes of this outlier and if such outliers exist within that lot or other close serial numbered reagents. The data analytics may also investigate other instrument issues both with the particular instrument that generated that reagent data point as well as the company's other instruments and all the instruments of its kind connected to the database system. Thus, quality assurance application 154 may assist in tracking down issues.

Figure 11:
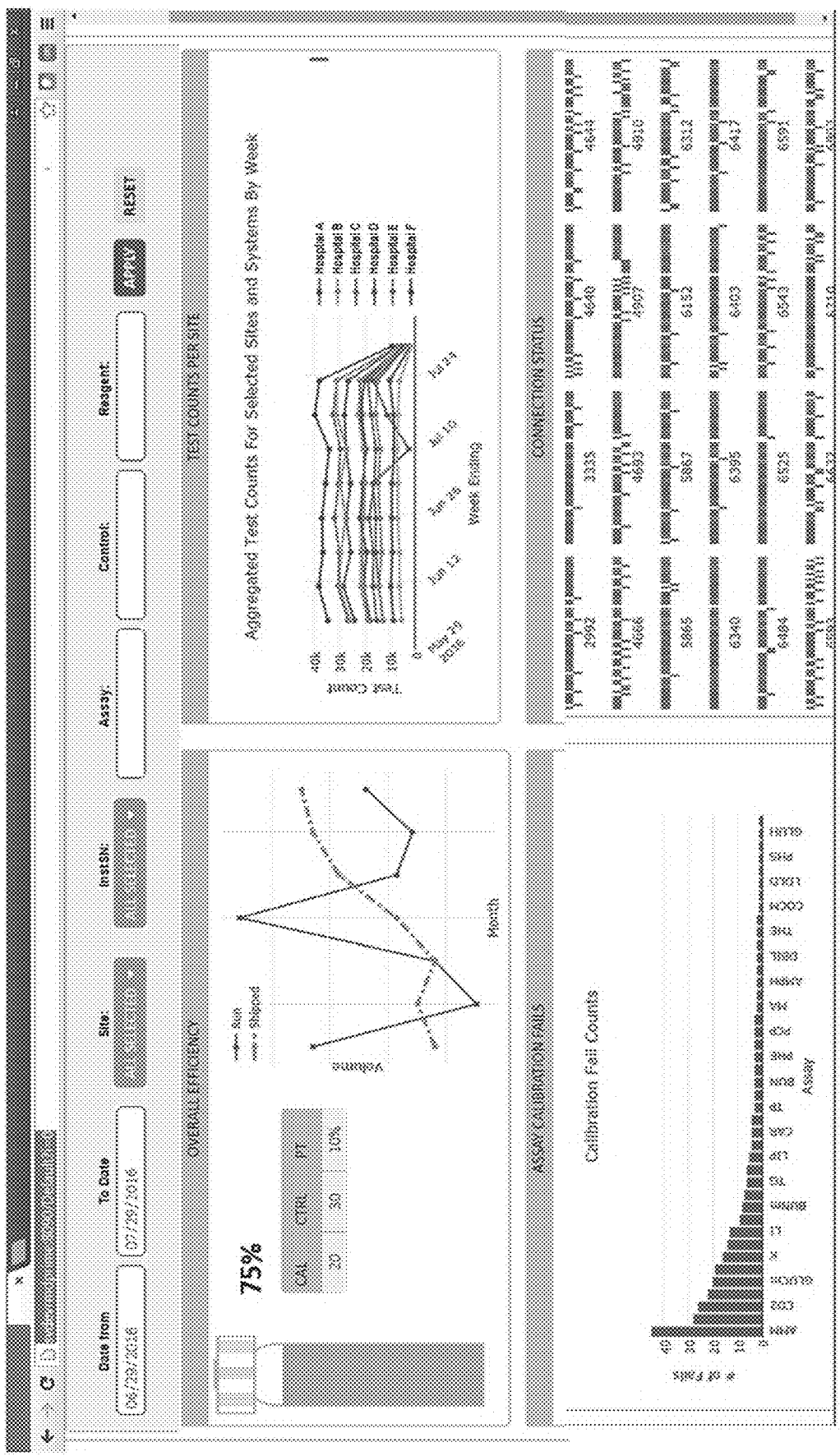
FIG. 11 is a screenshot of an exemplary interface presenting visualizations of multiple parameters which are relevant to the operation of analytical instruments.
Figure 18:
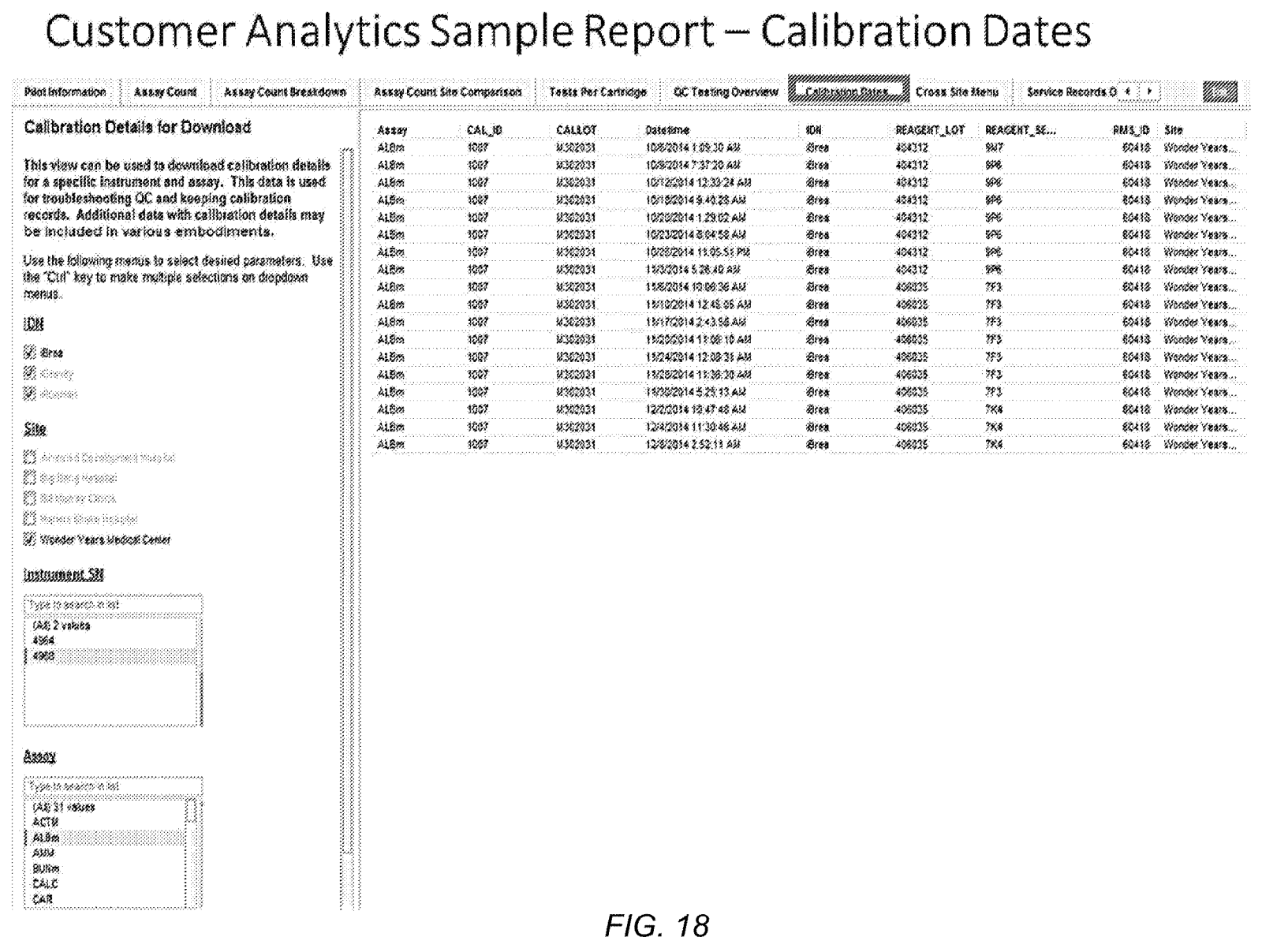
Figure 19:
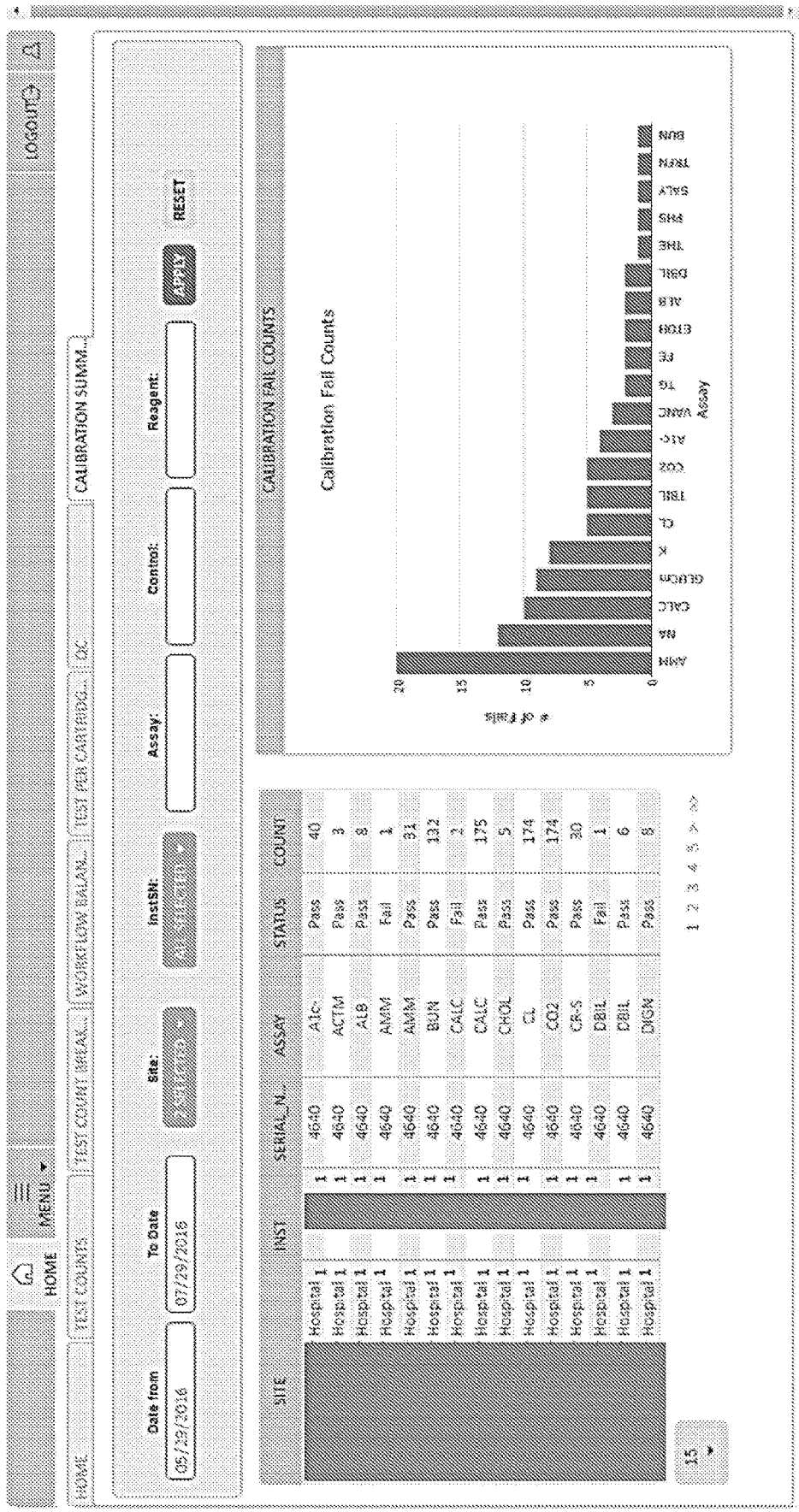

Other interfaces which could be used to present calibration information are provided in FIGS. 18, 19 and 11. In the interface of FIG. 18, the user would be presented with information on dates and times when calibration took place, that may be downloaded and used for troubleshooting, recordkeeping and/or other purposes. FIG. 19, provides calibration information in a graphical format, with a bar graph showing calibration failure counts for particular types of assays, and a textual table providing additional details such as the status of the relevant instrument(s). FIG. 11 presents an exemplary dashboard interface which includes a bar graph with calibration fail count information such as shown in FIG. 19, as well as other information relevant to the operation of analytical instruments, such as the number of counts per site and their connection status. Preferably, an interface such as shown in FIG. 11 may be customizable based on user preferences, so that each user may see at a glance all information that he or she believes may be most relevant to his or her particular responsibilities with respect to the instruments in question.

A reagent as used herein may describe virtually any consumable for an analytical instrument. For example, a reagent may be a mobile phase, a buffer, a rinse solution, a purified water, a compressed gas, cooling liquids (e.g., liquid nitrogen), or the like.

In other embodiments, database 102 may host a remote diagnostic application 156 wherein diagnostic data about the instruments may be viewed by those with access to interface 150.

Remote diagnostic application 156, for example, may function by instruments 114 selecting and sending preselected data to RC device 112. RC device 112 in turn may transmit instrument data to database 102 via a secured, encrypted connection 110. Once the data is received at database 102, it may be saved and further processed by at least one processor. For remote diagnostic application 156, instrument operational data may be sent to RC device 112, and RC device 112, in turn, may send the data to database 102 wherein the data may be viewable by a user at interface 150 through remote diagnostic application 156.

In one embodiment, the features of remote diagnostic application 156 may be grouped into three main types: 1) Reactive Diagnostic, 2) Intelligent Diagnostic, and 3) Interface features. The Reactive Diagnostic feature may allow a user to view an instrument status and troubleshoot instrument issues. The Intelligent Diagnostic feature may allow the system and the remote users to predict and control the connected instruments. The Interface feature may allow the instrument user to network and upgrade their instruments.

Two functionalities of the Reactive Diagnostic feature may be a system health data transfer and a dashboard. The system health data transfer function may enable remote diagnostic application 156 to capture multi-parametric information regarding the health and performance of a connected instrument and to stream this data to database 102. This data stream may feed the remote diagnostic application 156 interface 150, e.g., a dashboard, and may trigger functions to predict failure alerts.

The dashboard may be a main remote diagnostic application 156 user interface. The dashboard may provide a real-time or near real-time summary of an instrument's health. The dashboard may provide a real-time or near real-time monitoring of instrument status, rapid remote diagnosis of issues, and/or detailed troubleshooting information. Algorithms in the server(s) may provide the dashboard with an organized stream of data, which may describe the health of the instrument, and may translate this data into a readable format.

In some embodiments, a service provider user may review any connected instrument using remote diagnostic application 156 and may immediately assess system status when troubleshooting on the phone with an instrument user. Overall, the dashboard may give a remote diagnostic application 156 user a detailed view of system health and may facilitate troubleshooting, as if a technical support representative was on site.

The intelligent diagnostic feature may allow prediction and control of the connected instruments. These functionalities of the intelligent diagnostic feature may include: remote desktop sharing (RDS), triggers, and remote system adjustment. With RDS, a user may view and take control and view remote instrument status and initiate a troubleshooting process. Triggers are proactive algorithms that monitor incoming instrument data and alert support personnel of potential instrument issues. Remote system adjustment may allow support personnel to adjust the remote instrument hardware and/or software using RDS.

The Interface feature may allow users to upgrade an instrument via remote data collection pipeline.

In some embodiments, quality assurance application 154 and remote diagnostic application 156 may run together. In other embodiments, they may run separately. In one embodiment, quality assurance application 154 and/or remote diagnostic application 156 may track standard curves of various instruments and determine if the standards run on the instruments are within an acceptable range. Thus, an instrument may know that its standards are out of acceptable range and may order a technician to service the instrument before the instrument user may even know. In other embodiments, the applications may be used to automate the standardization process. In other words, an instrument may know when its standardization is not acceptable and may order a technician or order a serviceable part for the instrument without an instrument user's input.

In one exemplary embodiment, quality assurance application 154 and/or remote diagnostic application 156 may track operating temperatures of remote instruments. This data may be used by the processor in the database system to track trends such as heater function, energy usage, cooling fluid levels, and/or heater system malfunctions. Again, the database systems through analysis of the rich data may know when an instrument's heating system is not working efficiently or properly and may order a technician a serviceable part for the instrument without an instrument user's input.

In both cases, quality assurance application 154 and/or remote diagnostic application 156 may assist in streamlining instrument function and prevent downtime from unscheduled instrument outages.

Further still, quality assurance application 154 and remote diagnostic application 156 may work together with the database and the data analytics program or module to identify stochastic phenomenon that may exist in instruments on a more global scale that can only be identified by looking at a complete or substantially complete set of rich data and analyzing it for potential anomalies. The at least one processor in the database system may achieve this goal by executing the data analytics program or module to analyze the big, rich data database housed on the servers described herein. A case study is described in Example 1 where a database system as described herein was used to resolve a multifaceted stochastic phenomenon that resulted in flow cell failure in an analytical instrument.

Further still, database 102 may host a metering application 158 wherein consumable levels and data from the instruments may be viewed by those with access to interface 150. This metering application 158 may provide proactive replacement of consumables to prevent unplanned stoppage of workflow or inaccurate results due to depletion of a consumable.

Figure 4:
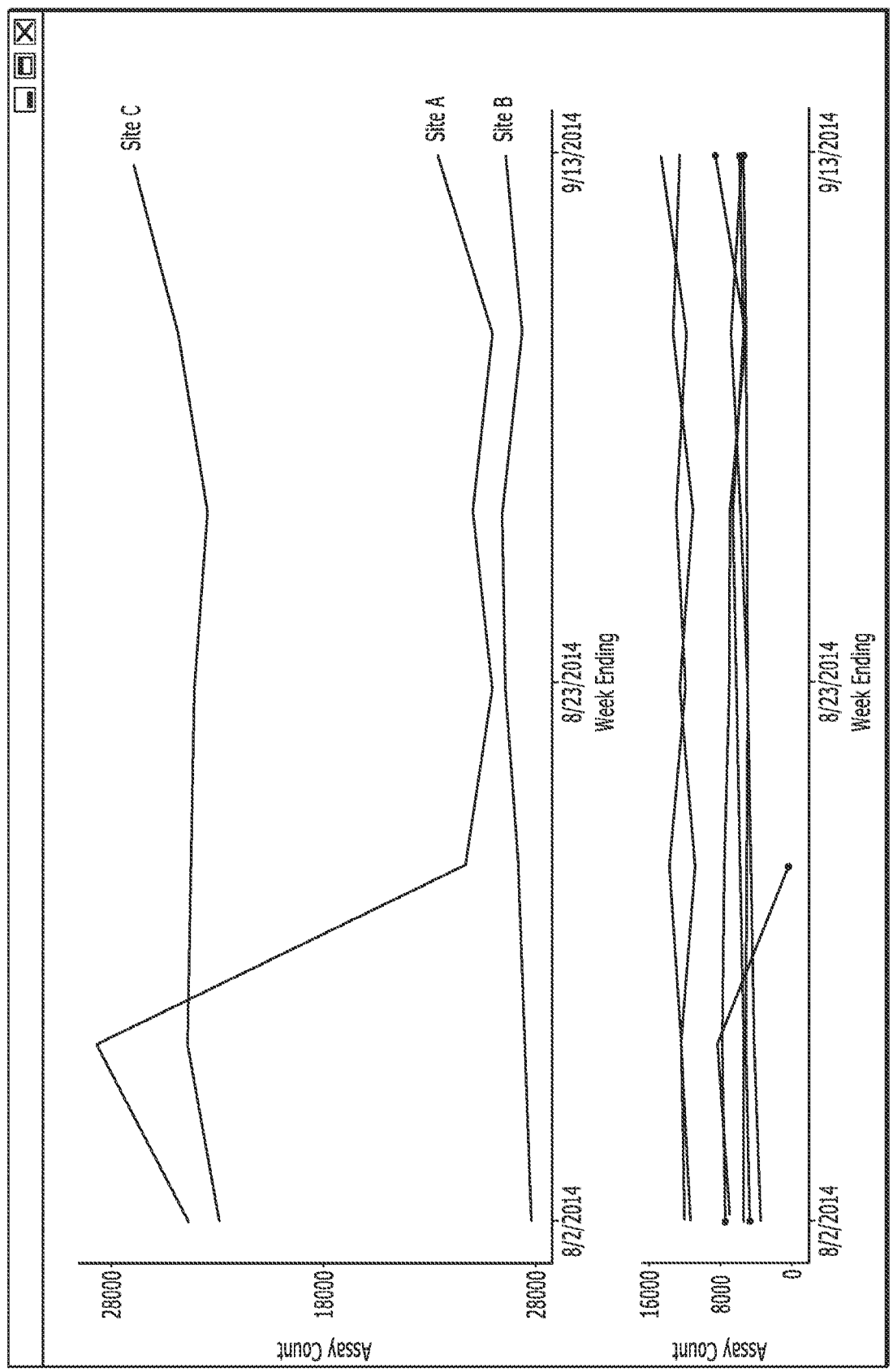

An example interface screenshot is illustrated in FIG. 4. This screenshot shows assay count per instrument per site within a user's network. As an example, in FIG. 4 this user has three sites with instruments, site A, site B and site C. It is understood that more or less than three sites may be included. For example, two, four, five, six, seven, eight, nine, ten, eleven, twelve, 13, 14, 15, 16, 17, 18, 19, 20, or more sites may be included.

The top graph in the screenshot shows that site A had an initial surge of samples run and then fell off drastically. Site C on the other hand has had a more constant higher volume sample turnover and site B generally has a low turnover. A user viewing the sample counts over time for the three sites may shift samples between locations to balance workflow. For example, some of site C's samples may be shifted to site B to balance workflow between the two sites. On the other hand, when site A has a surge of samples pushing it toward capacity or over capacity, samples may be shifted to sites B or C as needed depending on their particular workflow.

Figure 12:
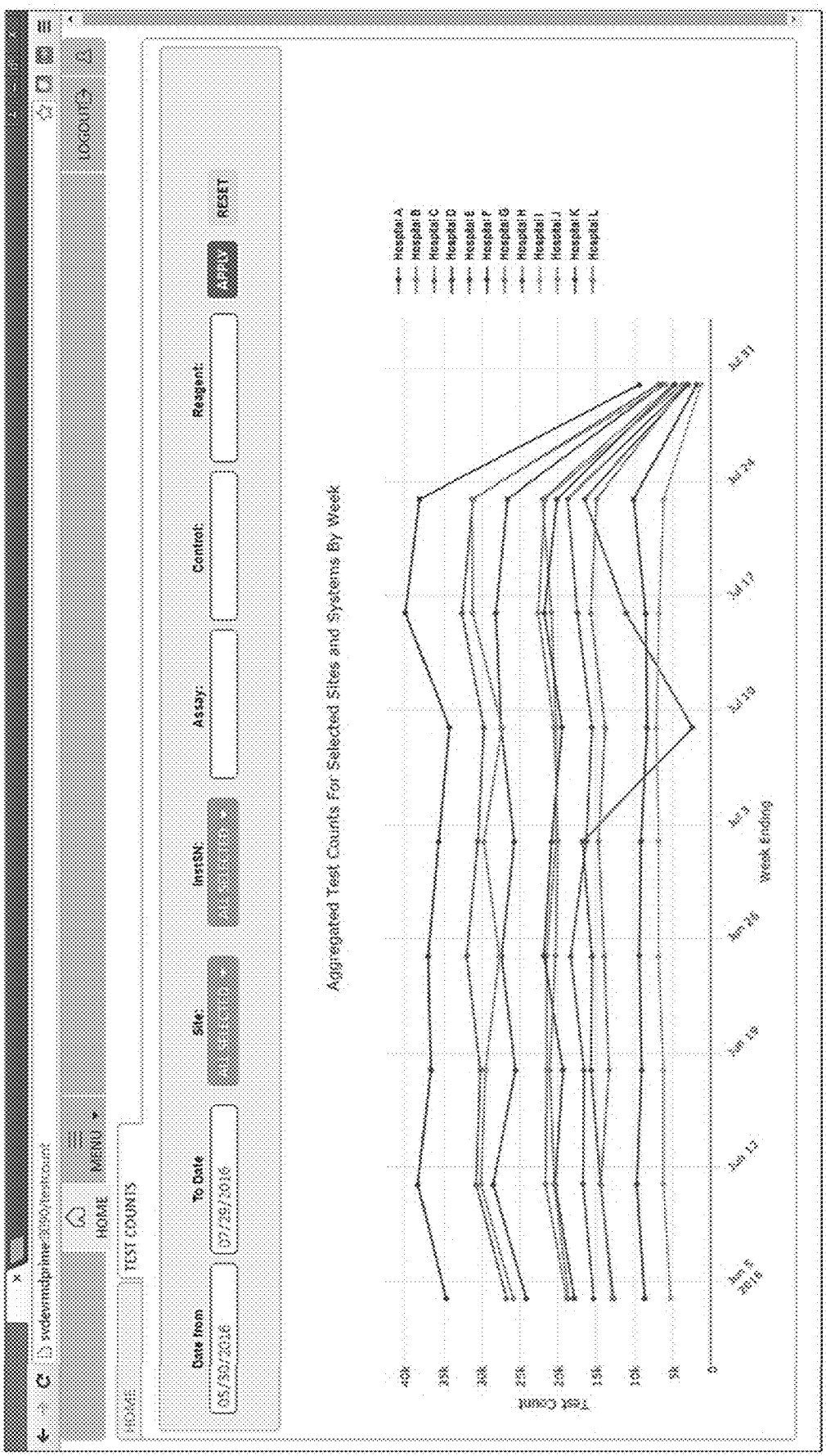
FIG. 12 is an exemplary interface presenting test count information for multiple sites.
Figure 13:
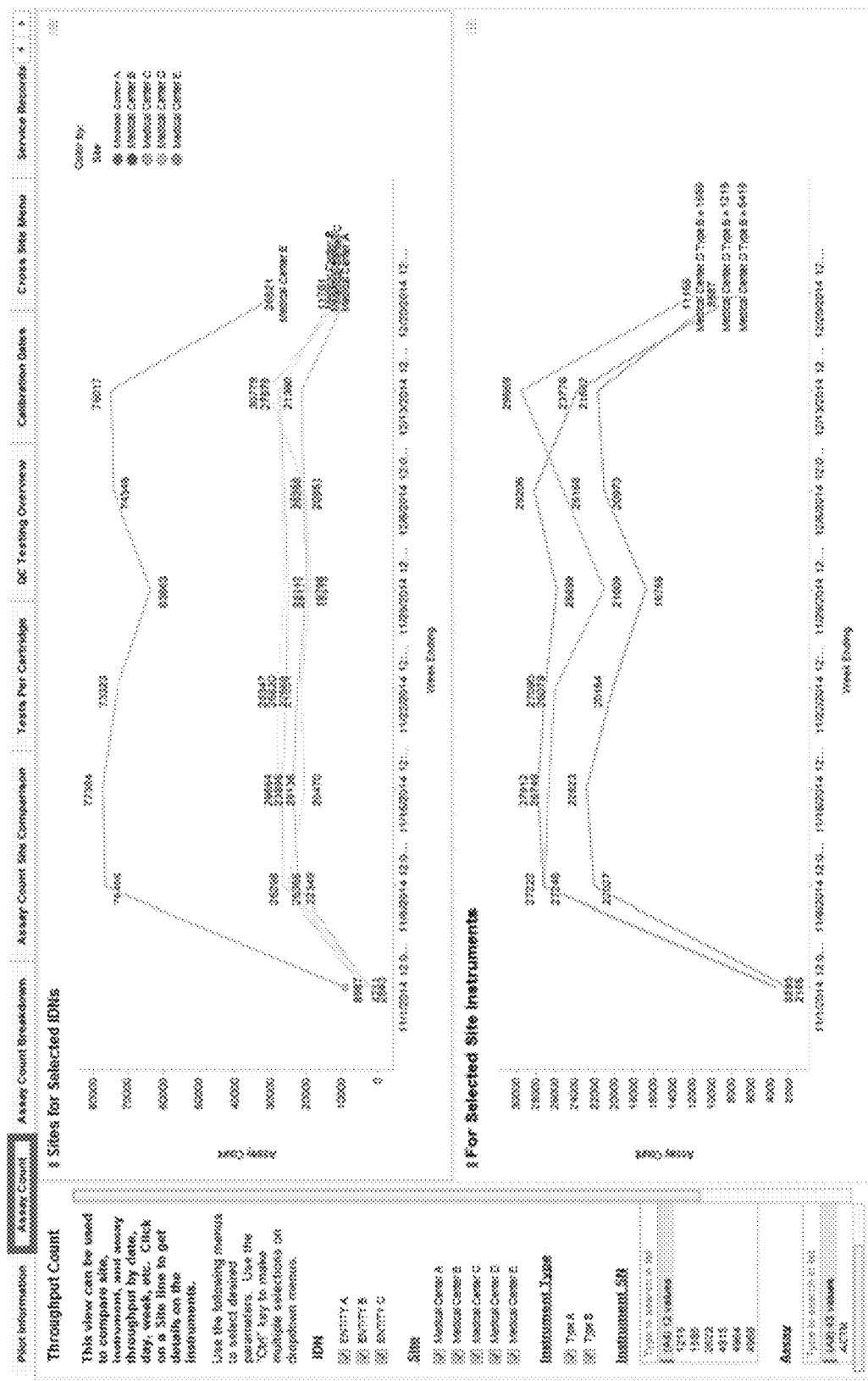
FIG. 13 is an exemplary interface presenting test count information for multiple sites, along with test count information for particular instruments at a particular one of the multiple sites.
Figure 25:
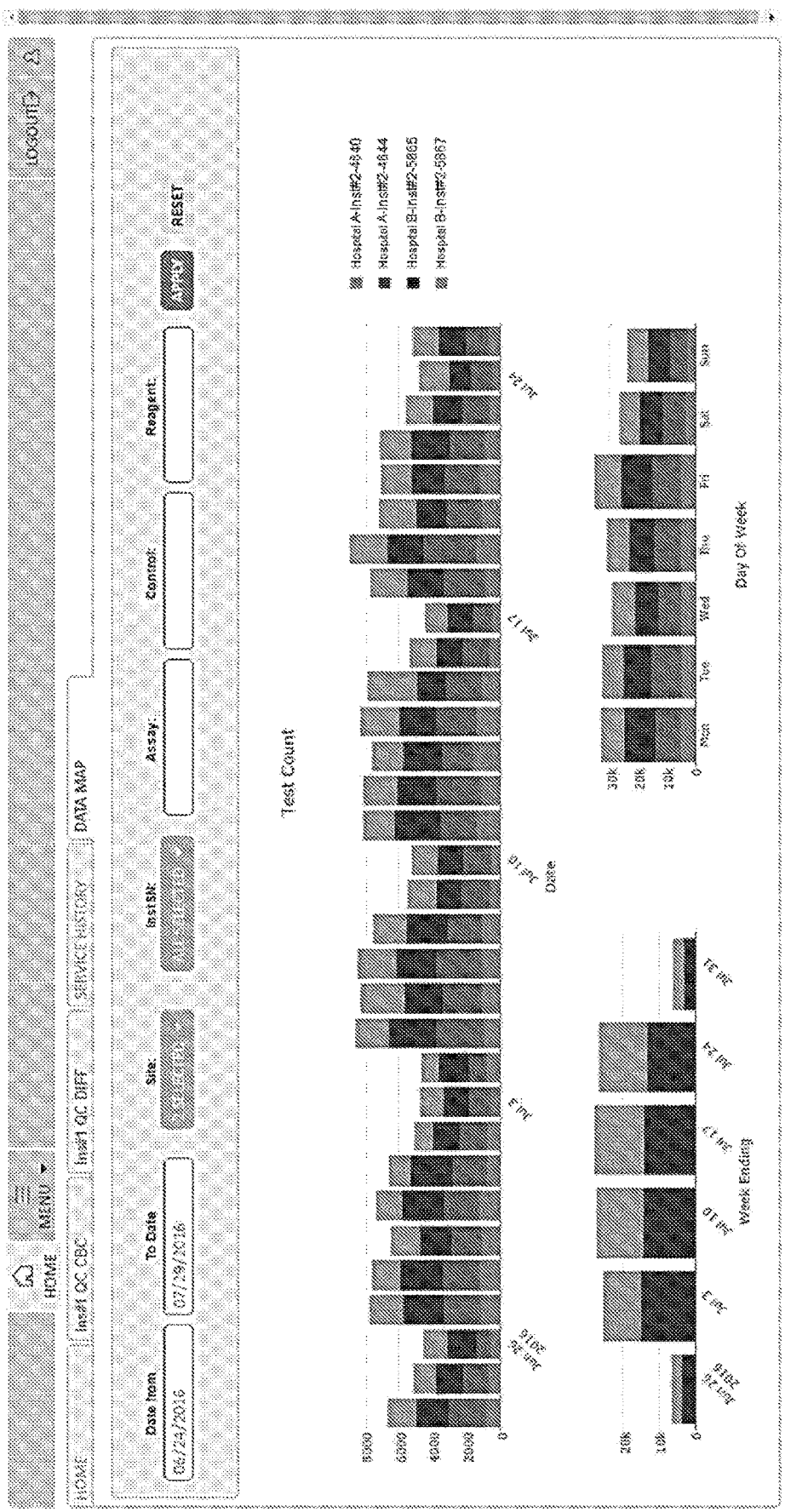
FIG. 25 is an exemplary interface which may present test counts per day for particular sites and instruments in a color coded manner.
Figure 26:
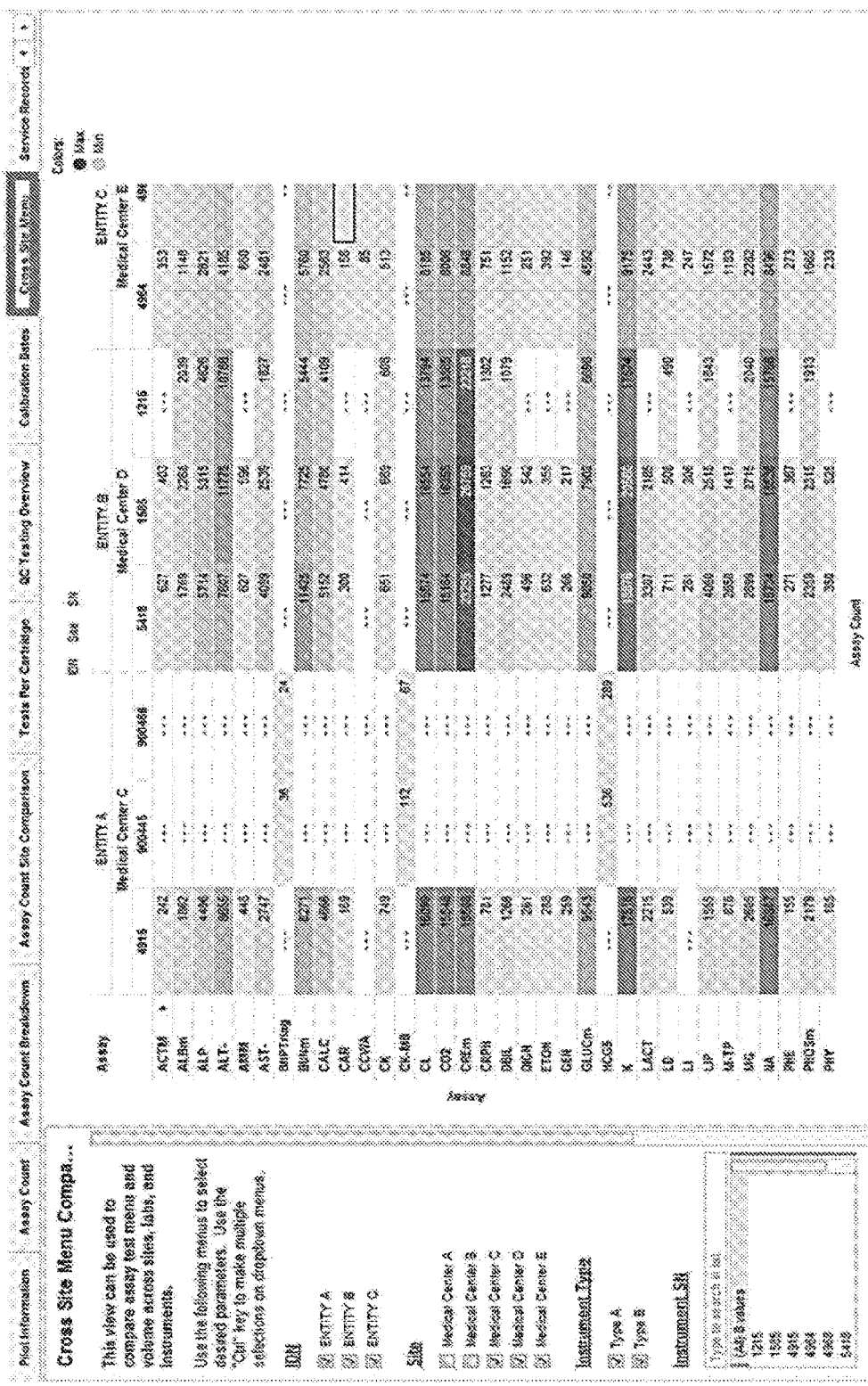
FIG. 26 is an exemplary interface which presents test count information as well as information which can be used in cross site comparisons of menus of available tests.

Further examples of interfaces which may present assay count information are provided in FIGS. 12, 13, 25 and 26. In FIG. 12, a line graph (which, in practice, would preferably be shown in color) is shown presenting information regarding the number of test which were performed at each site selected by the user to whom the interface is presented (which, in the case of FIG. 12, is all sites which that user has authority to access). In FIG. 13, a similar line graph is presented (which, as with FIG. 12, would preferably be presented in color), along with a second graph, presented below the first, showing the number of tests performed on specific instruments located at a particular one of the sites whose total counts are presented in the first graph. FIG. 13 also includes a sidebar with controls which may be used to specify the type of information which would be presented in the illustrated graphs, as well as a description of the information which is included in those graphs. FIG. 25 illustrates the number of tests performed on a daily, weekly and day of the week basis, using color to indicate tests performed on specific instruments at particular sites. FIG. 26 presents a table interface which shows not only numbers of tests performed using particular instruments, but also indicates the menus of tests available on those instruments for use in cross-site capability comparison. Further the graphs and other interfaces can be used to predict workflow for sites based on historical trends in workflow or even looking forward from current trends.

Figure 5:
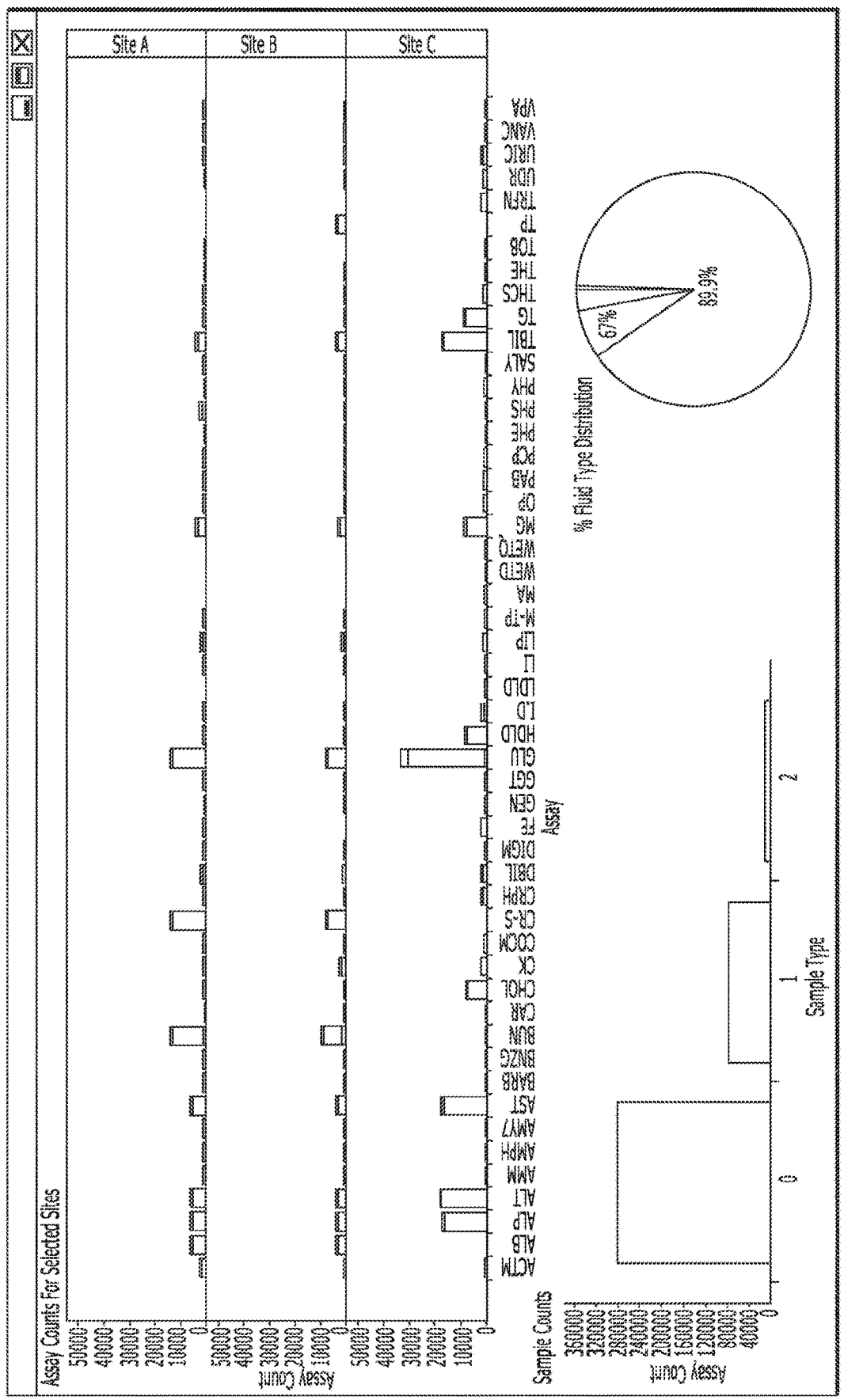

FIG. 5 illustrates an alternate view of a screen shot from the same three sites as FIG. 4. FIG. 5 shows the number of each particular assay run at each site in the upper set of bar graphs. Thus, in addition to seeing sample count over time from FIG. 4, FIG. 5 may allow a user to see what particular assays are being run to arrive at the total assay count. This data may help further fine tune workflow. For example, where sites A and B are high in a particular assay, site C although higher, workflow over all is lower in this particular assay. Thus, this particular assay may be shifted between locations to better balance workflow.

The bottom left bar graph in FIG. 5 shows total overall sample volume for samples (PT), quality control (QC) and standardization (Cal). This graph may help a user understand how efficient their sample runs to quality control/standardization ratios are to shift them accordingly.

Figure 14:
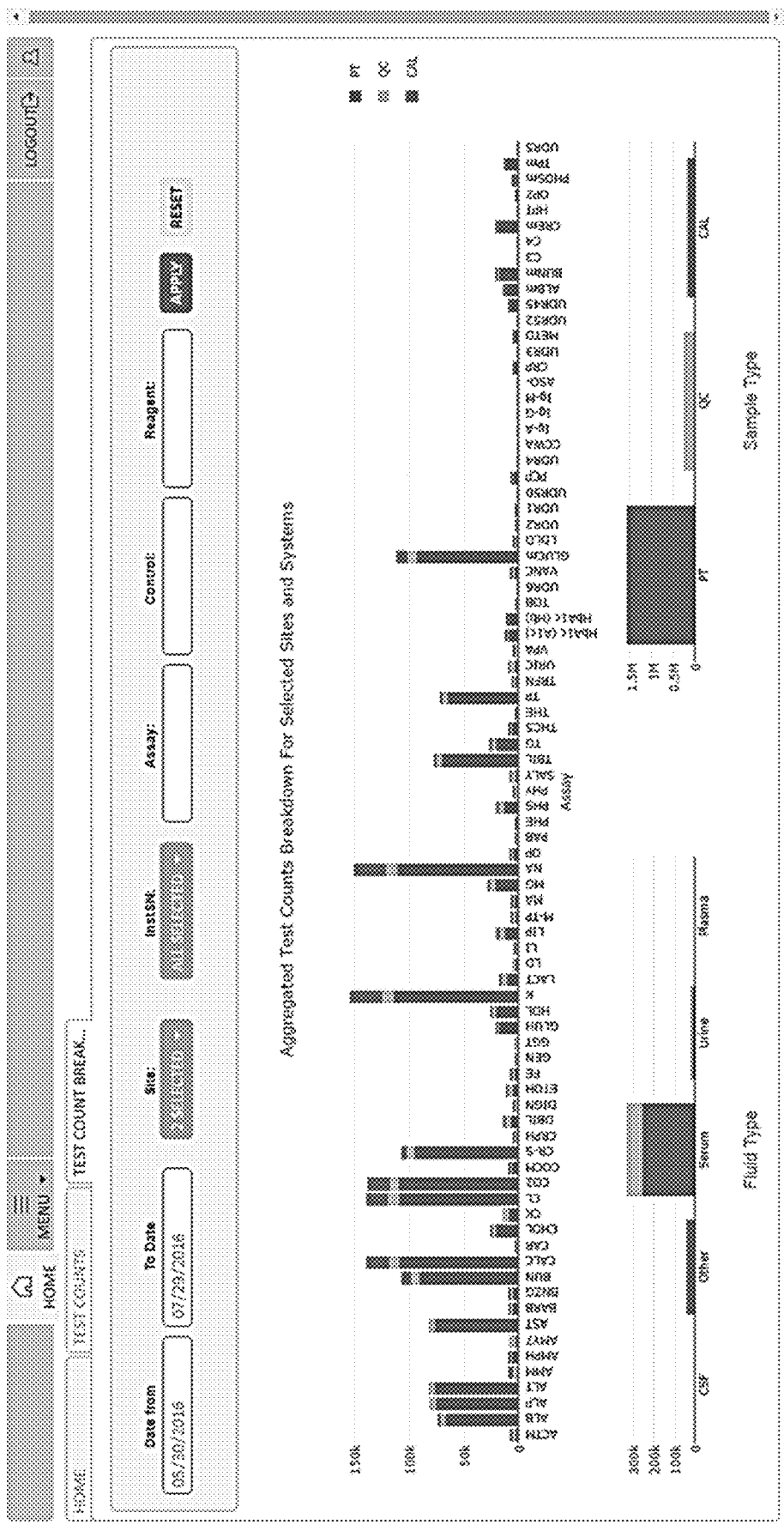
FIG. 14 is an exemplary interface which presents assay count information broken down by assay type and which may use color to illustrate sample type.
Figure 15:
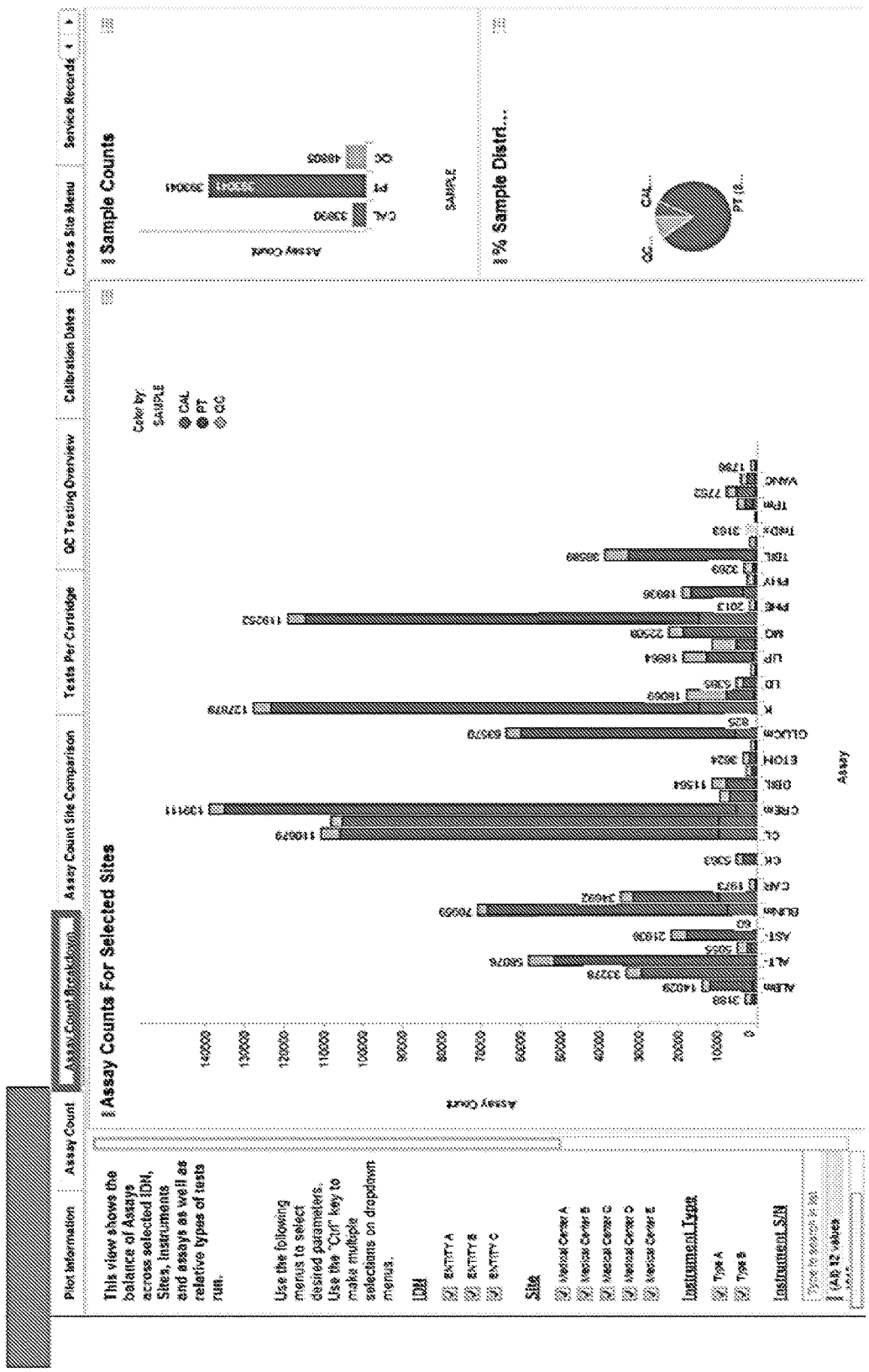
FIG. 15 is an exemplary interface which presents assay count information broken down by assay type and which may use color to illustrate sample type.

The bottom right graph in FIG. 5 shows overall fluid types being processed by the three sites. Here, serum is the largest. The system or a user may allocate other types of fluid testing to other types of instruments or other locations not shown here to balance workflow. For example, the urine sampling may require an extra worker that might otherwise be eliminated if the samples were outsourced or moved to a different location. Further, a particular new instrument may be able to offload that portion of assay count. Additional interfaces which present assay count information, broken down to indicate particular assays are illustrated in FIGS. 14 and 15. In FIG. 14, this information is presented in three bar graphs, one illustrating particular assays, one indicating types of fluid, and one indicating the particular types of samples (i.e., PT, QC or CAL). In FIG. 15, this information is presented in a bar graph indicating assay type, a bar graph indicating sample type (i.e., CAL, PT or QC), and a pie chart indicating the distribution of sample types. Interfaces such as shown in FIGS. 14 and 15 would also preferably be implemented to use color to indicate sample type in the bar graphs for assay and fluid types, thereby providing a convenient way for a user to immediately perceive information which could be used for identifying and responding to anomalies on workload (e.g., in the graph of FIG. 14, the fact that almost all of the assays which were not used for testing serum, urine, plasma, or CSF were used for calibration would preferably be reflected through the use of a particular color, such as solid pink, for "other," thereby allowing a user to modify the relevant workflows, such as by routing more additional types of tests to the relevant instrument, or decreasing the test menu which would be maintained on that instrument).

Figure 6:
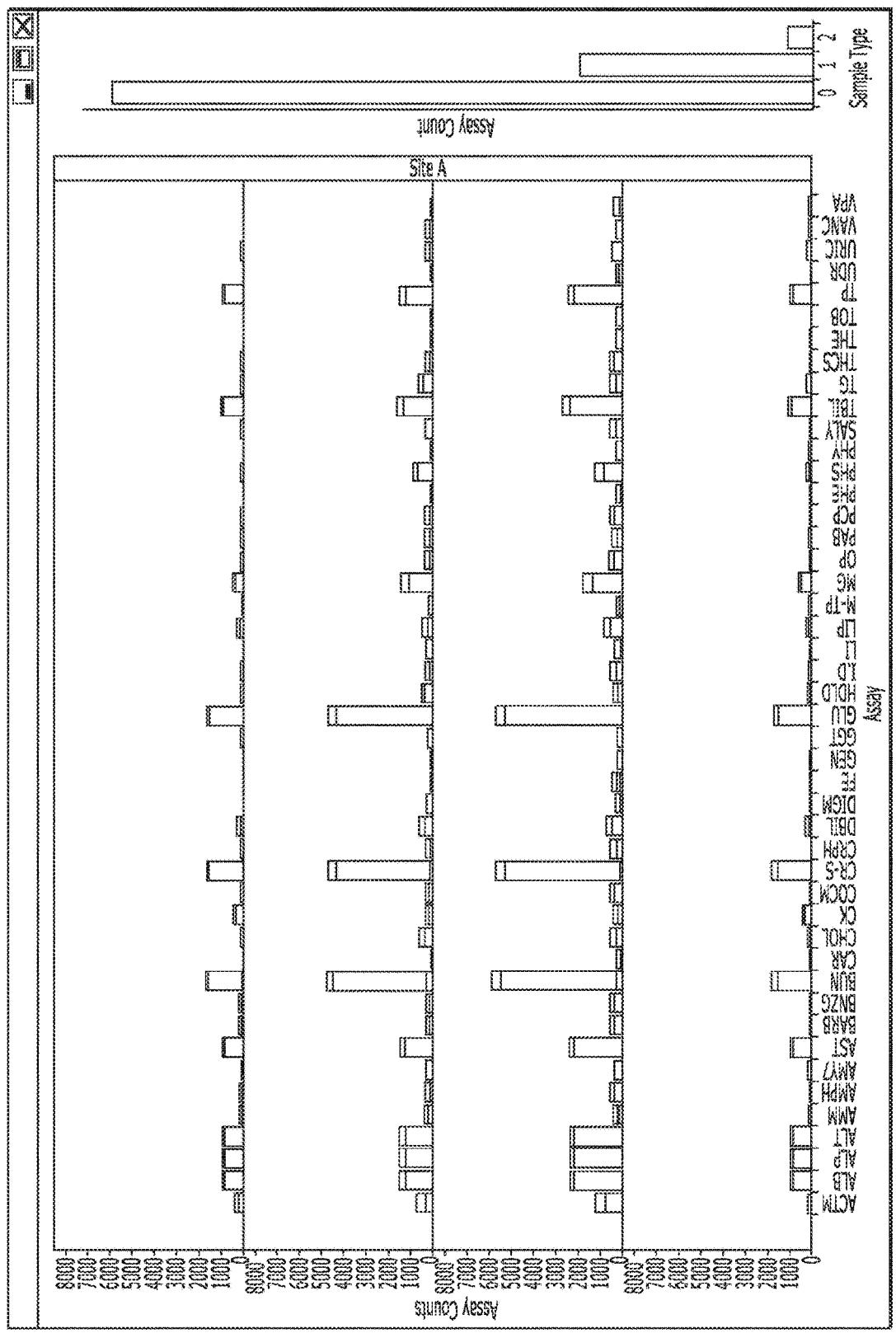

FIG. 6 illustrates a screenshot of a single site's (site A) distribution of assays run on four different instruments there. This screenshot may be useful to reallocate samples to different instruments to balance workflow between the instruments. For example, instruments 2 and 3 may be performing substantially more assay than instruments 1 and 4. Thus, workflow may be shifted from instruments 2 and 3 to instruments 1 and 4 to balance workflow.

Further, if an instrument at a particular site has a lesser calibration potential, e.g., is not calibrated as well or is an older machine, workload may be reduced on this machine or lower priority samples may be run on this machine. Lower assay counts on an older machine may potentially increase its effective lifetime by not overtaxing an older instrument.

Further still, if a particular instrument breaks and/or needs service, FIG. 6's screen may be effective for moving workflow to a different machine that has overhead to spare. Moving assays from a broken instrument to a less utilized instrument with overhead to spare may prevent a laboratory stall. In one embodiment, the database server may automatically execute a program that may determine which instrument has spare overhead and shift assays to that instrument(s). Thus, the database systems described may assist in preventing laboratory downtime.

Figure 16:
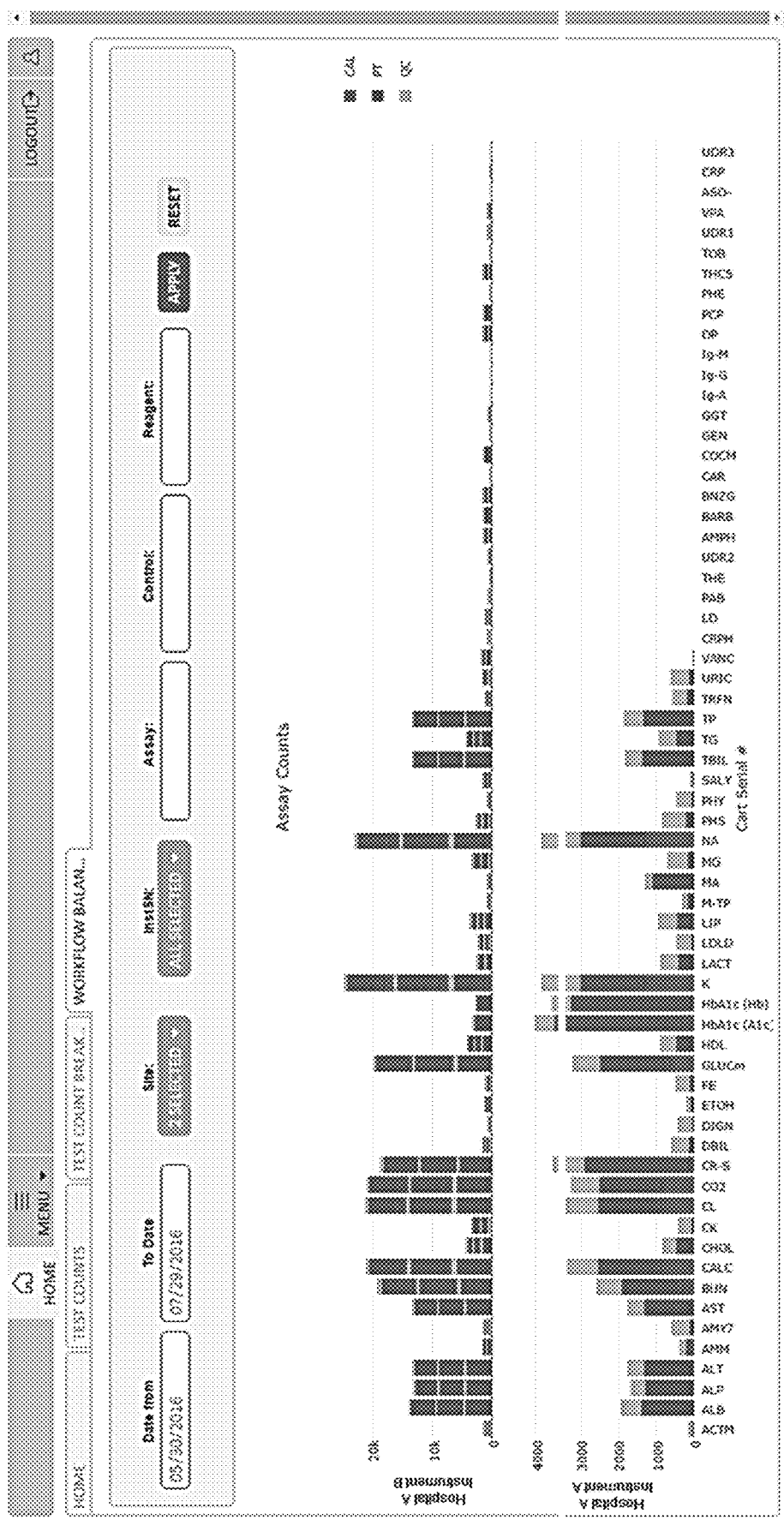
FIGS. 16-17 are exemplary interfaces which present information on distribution of assay runs at various sites.

An additional exemplary interface which presents information on distribution of assay runs at a single site is provided in FIG. 16. In FIG. 16, this information would preferably be presented with color coding such as previously discussed in the context of FIG. 14 to enable the user to distinguish at a glance between assays performed for samples, calibration and quality control. Additionally, the interface of FIG. 16 illustrates an approach to depicting an interface which may allow the user to tell the approximate frequency of the different types of activities. For example, in an implementation of FIG. 16 which includes color coding, a bar which begins with a relatively long blue bar, followed by a slim green bar, followed by a relatively long blue bar, followed by a slim green bar, followed by a relatively slim pink bar, followed by another relatively long blue bar might indicate that a large number of samples were tested by the instrument (represented by the first blue bar), followed by a quality control test which confirmed that the instrument was still functioning as expected (represented by the first slim green bar), followed by another large number of samples being tested (represented by the second blue bar), followed by a quality control test which indicated that the instrument needed to be recalibrated (represented by the second green bar), followed by recalibration (represented by the pink bar), and then another large number of samples being tested (represented by the final blue bar).

Figure 17:
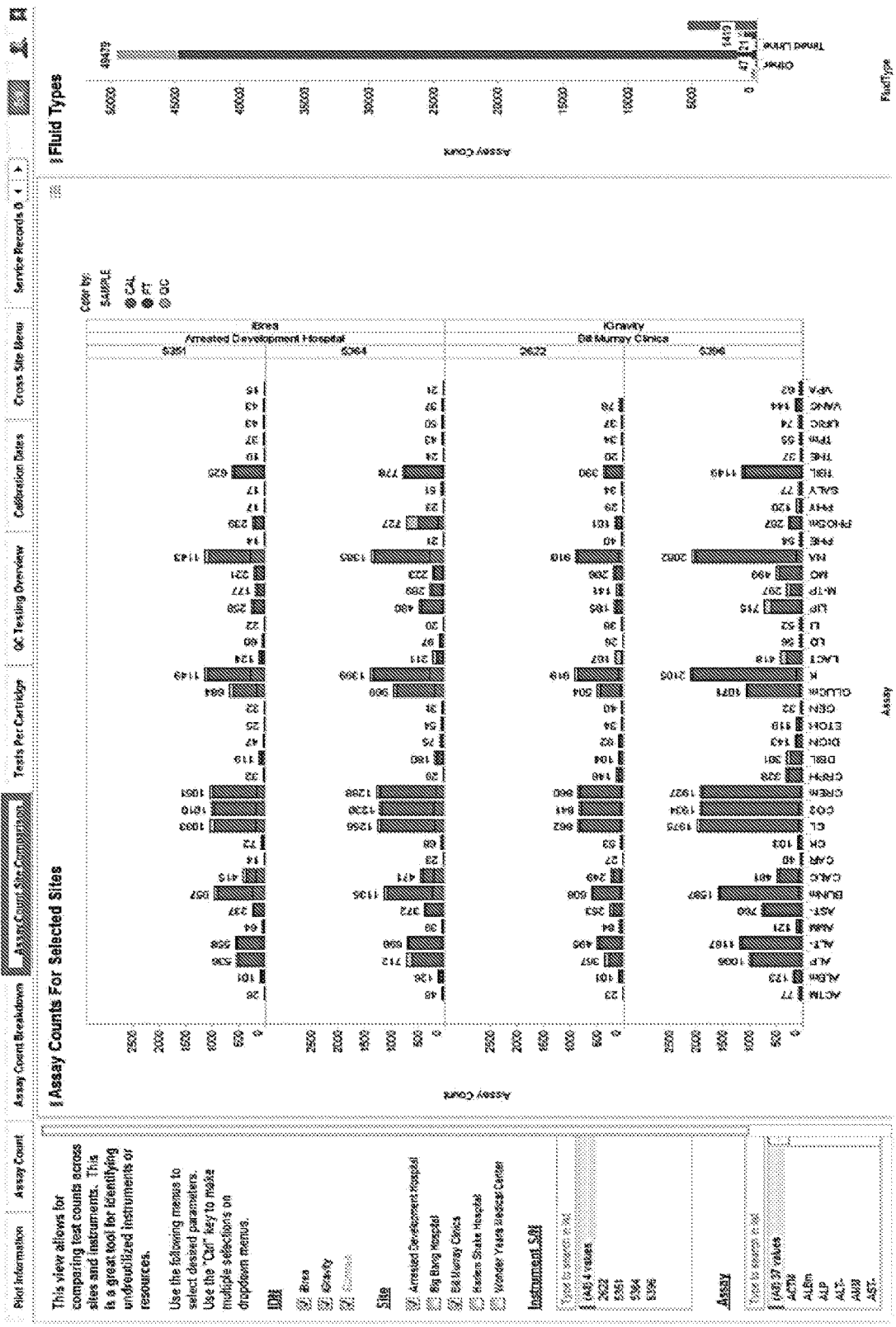

Yet another exemplary interface which may present information on distribution of assay runs at various sites is provided in FIG. 17. In that interface, which could use a similar type of color coding as discussed in the context of FIGS. 14 and 16, the user is not only enabled to compare instruments within a single site, but may also be enabled to quickly compare information across different sites run by a single entity, or even between different entities. With this type of functionality, a third party service provider (e.g., an instrument manufacturer) who is responsible for multiple instruments might use the information from its entire client base to quickly identify trends or common practices. This might then be used for purposes such as proactively identifying and initiating remediation measures for problems, or generating anonymized benchmarks which might be provided to individual customers to enable them to evaluate their practices against peer group averages. Of course, other uses, such as allowing customers to identify workflow issues (e.g., an instrument which is using an inordinate amount of its assays in calibration, or a bottleneck resulting from a particular type of assay being allocated almost exclusively to a particular machine) are also possible and will be immediately apparent to those of ordinary skill in the art in light of this disclosure. Accordingly, the discussion above of FIGS. 16 and 17, like the discussion of the remainder of the figures in this document, should be understood as being illustrative only, and should not be treated as limiting.

Figure 7:
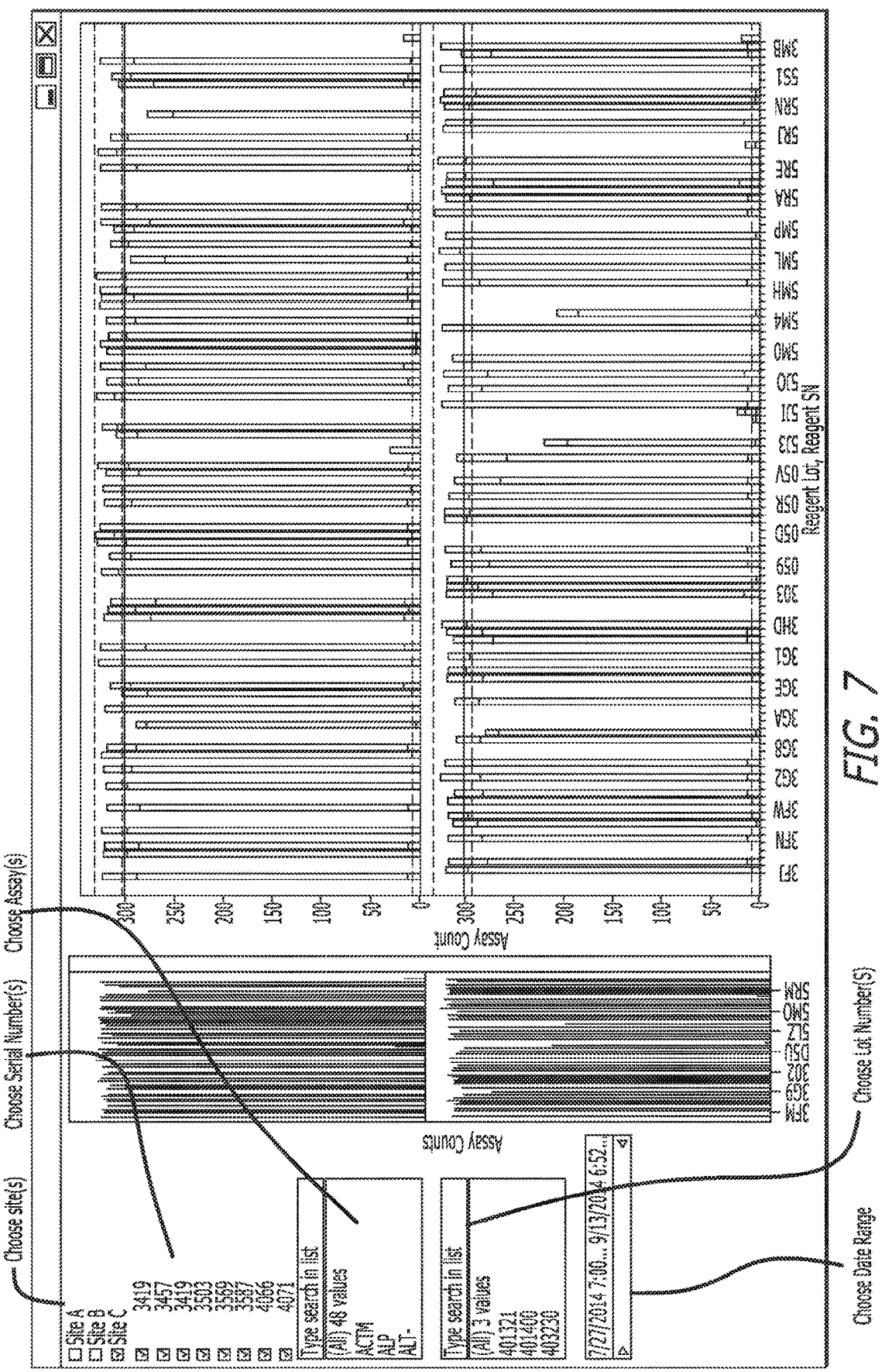

FIG. 7 illustrates a screenshot of a single site's (site C) distribution of reagent usage on two different instruments. Further, reagents may be separated by lot number and/or serial number. Lines showing average reagent usages may assist in determining if more or less than usual reagents are being used, for example, to calibrate an instrument. In one embodiment, this data may be used with other applications, such as quality assurance application 154 and remote diagnostic application 156 to determine if more than normal amounts of calibration or quality control reagents are being used which may be indicative of a dirty detector/source or a detector/source that is malfunctioning. Thus, metering application may interface with quality assurance application 154 and/or remote diagnostic application 156 to proactively remedy an instrument fault before it occurs.

Further, reagent data may be used to shift workload between instruments to efficiently utilize reagent and instrument lifetime.

FIG. 7 also illustrates how the interface is used. A user may be enabled to select a particular site where the instrument(s) are located. Here, only site C was selected. But, in other instances, other sites may be selected in various combinations. Then, based on the instruments at a selected site, specific instruments may be selected. Here, instruments are listed by serial number, but other identifiers may be used. Then, any number of assays may be selected for display. Here, no assays were selected as only reagent use is displayed. Then, reagents may be chosen. Here, reagents are shown by lot number, but otherwise may be labeled by serial number, type, etc. Finally, a date range is chosen and the data is displayed. In fact, the data may be dynamically displayed in near real-time as the different options are selected.

FIG. 8 illustrates a screenshot of a multi-site (site A, site B, and site C) distribution of reagent usage. The results are conveniently presented in table format. The table may be arranged by reagent usage per assay type per location. Cells may be colored or shaded with greater or lesser density depending on the number of assays run. A darker shade may indicate more runs and a lighter shade may indicate less runs. A white box may indicate that no assays were run with a particular reagent. A white or non-shaded box may make identifying non-run assays easier to spot. As can be understood shaded boxes may be varying shades of color of different colors altogether.

Thus, in some embodiments, as seen in FIG. 8, highly dense shaded cells (in practice can be different colors) may indicate high capacity and a potential need to shift workflow to a different instrument or to a different site. Likewise, a lesser shaded density shaded density may indicate that workflow may be shifted to this instrument from another instrument at that site or shifted from another site. Again, a processor in the database system may execute a program to shift workflow as required, desired, and/or discovered by the database system.

Figure 20:
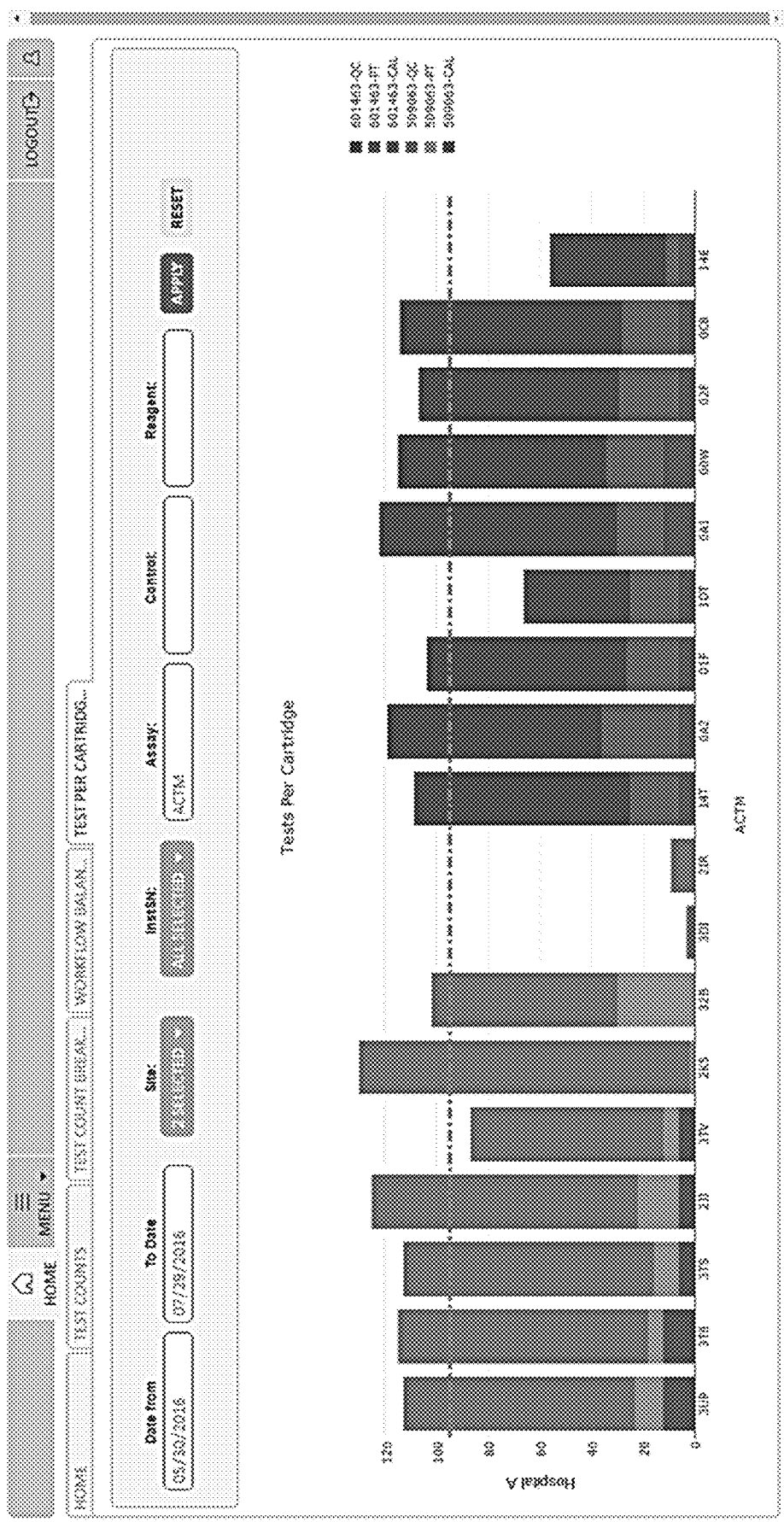
FIGS. 20-21 are exemplary interfaces which present reagent usage data.
Figure 21:
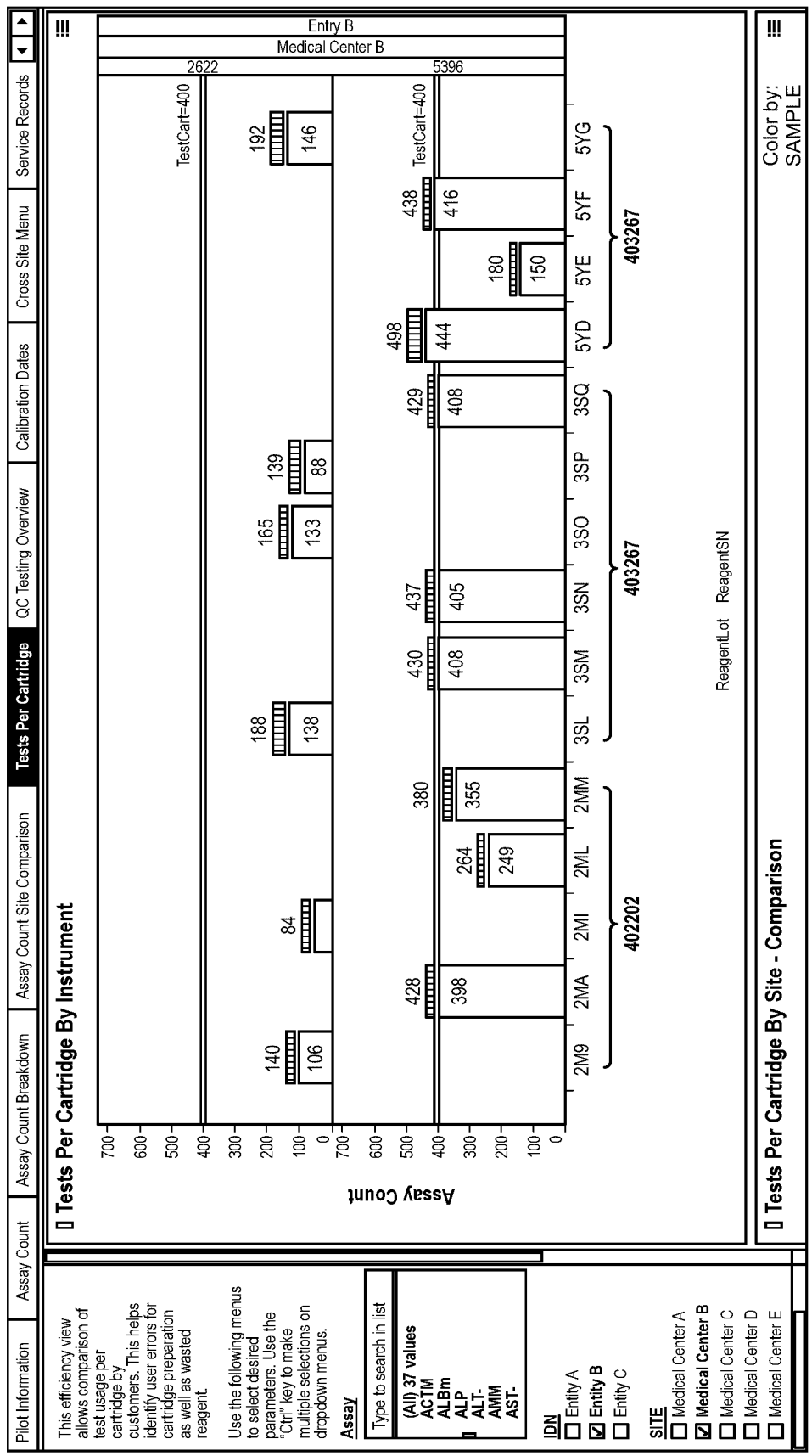

Additional examples of interfaces which may present reagent usage data are provided in FIGS. 20 and 21. Starting with FIG. 21, that figure shows numbers of tests performed using particular cartridges with individual instruments at a particular site, and could use the same color scheme as discussed previously in the context of FIGS. 14 and 16-17 to allow a user to easily distinguish between usage types. FIG. 20 also presents information regarding the number of tests per cartridge at a particular location, but differs from the diagram of FIG. 21 in that it could use separate color schemes to allow a user to distinguish both usage type and the cartridge(s) to which the data in the interface relates. Based on any of the data presented by the metering application, a particular site may desire to purchase a new instrument to fill a workflow void. Also, if peer labs can view another lab's assay workload (anonymously), they may desire to match that lab's instrument setup and purchase a similar line of instruments to match productivity levels.

In some embodiments, the at least one processor may automatically execute a program that can effectuate efficiencies in instrument workflow. For example, the processors may execute programs to automatically divert workflow from a particular instrument or even a particular assay when a reagent is being replaced or a particular sensor is not functioning properly. Likewise, the processors may execute a program to automatically move workload between instruments in a given lab environment to balance specific workflow needs.

In some embodiments, the processors may execute a program to shift workflow based on sample priority. In other words, the processors may shift a sample of lower priority to slower instruments, instruments with less accuracy, or older instruments.

Workflow as used herein may be used to describe sample volume through an instrument or through a site, or it may be used to describe lab personnel that need to monitor and process samples for analysis. For example, even though an instrument may be able to handle an additional 5% workflow to reach capacity that increase in 5% may require an extra worker or an overtime worker where simply shifting work to another site that would need an extra worker or pay a worker overtime may be more cost effective for a company. Thus, the graphs provided by the database systems described herein may help balance workflow between sites from both an instrument and personnel perspective.

A consumable may be a reagent such as a mobile phase, a buffer, a rinse solution, or the like. Metering application 158 may monitor levels of consumables on remote instruments and alert an instrument user that their consumable is about to run out and present an option to purchase more consumable. Metering application 158 may also predict consumable depletion based on patterns of usage. For example, if a hematology lab consistently uses more mobile phase solution to run sample at the beginning of every month, metering application 158 may present options to purchase more of that consumable when it is predicted that the instrument user will need it, even before the need occurs.

In another embodiment, database 102 may host a development application 160 similar to application builder 250 wherein instrument, part developers, laboratory users, and the like may view instrument data to incorporate into their design calculations, get access to rich data to develop disease diagnosis and prediction, and improve instrument or laboratory operational efficiency. Further, development application 160 may allow instrument manufacturers to build smarter machines based on data from current generation machines. Data from current generation instruments may be used to build machines that may train and advise technicians and even automate more lab functions.

In another embodiment, database 102 may host other applications 164 or "Apps" as described herein.

Interfaces as described herein may be accessed by a user, whether a service provider user or an instrument user via a computer, tablet, mobile device, or other computing device. Accessible data may be at least about 1 month, at least about 2 months, at least about 6 months, at least about 12 months, at least about 24 months, at least about 36 months, at least about 48 months, or more of data for a particular instrument or cluster or network of instruments.

Example 1

Case Study

Figure 23:
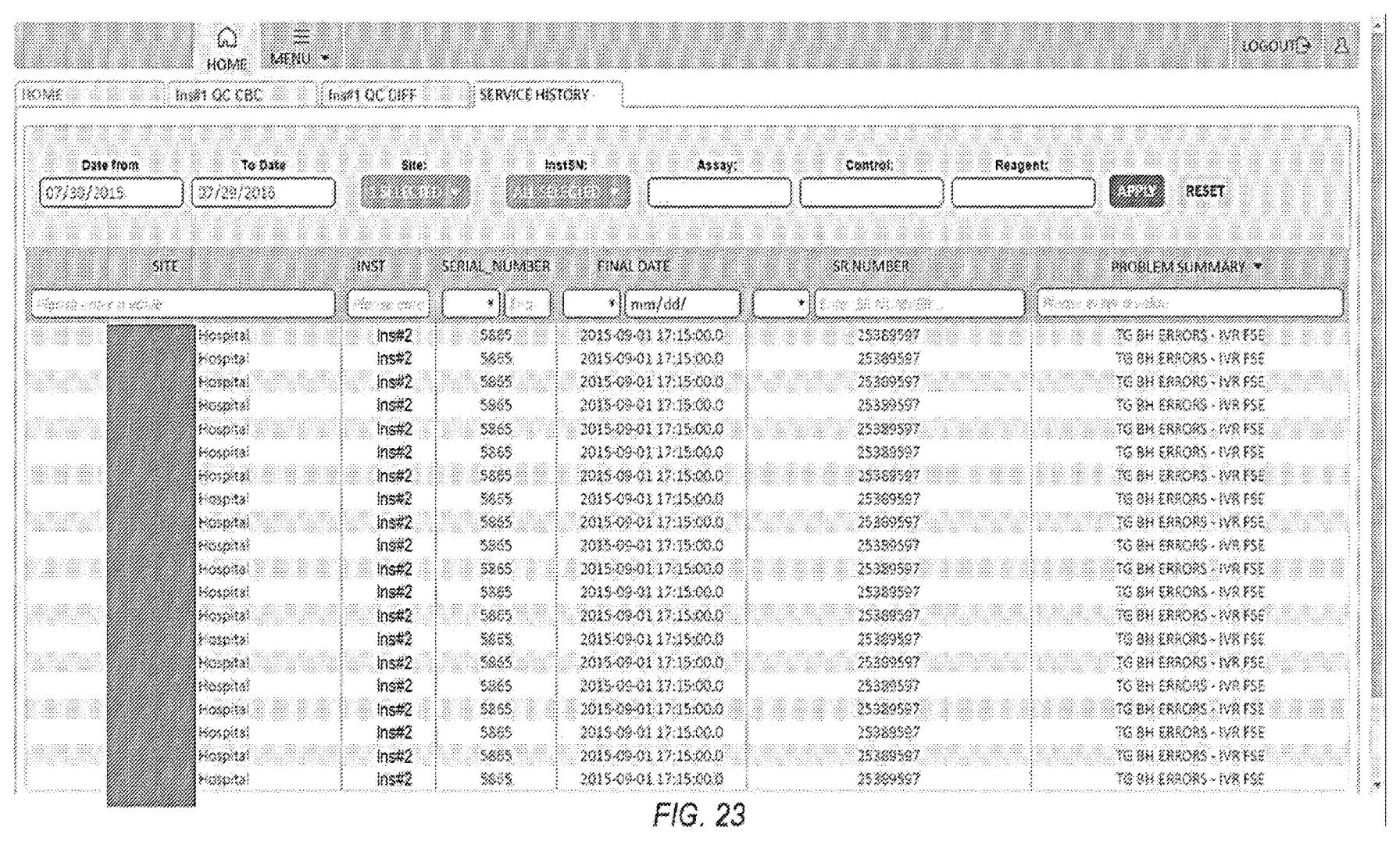

An instrument manufacturer sees a significant escalation in field service complaints regarding out of specification light scatter parameters in a line of analytical measurement instruments. This may be seen, for example, using interfaces such as shown in FIGS. 22 and 23, which present service history information for particular customers, sites, and instruments. This pointed to possible flow cell related failures, and an investigation was opened to address the escalating situation.

A goal became identifying root cause(s) and mitigating this issue became a priority because laboratories faced potentially affected results and instrument downtime and laboratory retention was at risk.

Flow cell failure is a phenomenon governed by many factors that can manifest in multiple ways. The issue was one thought to be a stochastic phenomenon, or one that is unpredictable because of the influence of a random variable. Various factors that can contribute to flow cell related failures may include those in Table 1.

TABLE 1

| Correlated Factors | |
| --- | --- |
| Hardware and Fluidics | Flow cell and fluidics system modifications. Possible unidentified changes in the flow. Unstable flow? Irregular cleaning cycles? |
| Reagents | Lot-to-lot variability A decrease in cleaning effectiveness? New inter-reagent or blood-reagent interactions? |

TABLE 1-continued

| Correlated Factors | |
| --- | --- |
| Software | Major software change, are there unidentified changes related to the flow cell? Is the diluter table effectively orchestrating flow and cleaning? |
| Probe and Coring | Tube-perforating probe design modifications. Are probes introducing more debris in the flow as they pierce the blood tubes? More imperfections in probe manufacturing? Has the tube stopper cap material changed? |
| Variability | Inherent instrument-to-instrument variability: age, usage, maintenance, calibration. Blood samples: fresh, aged, refrigerated, normal, abnormal. Human factor: Variability in instrument operation. |

Thus, a solution was required that could account for any and all factors that could potentially cause the flow cell related failures.

Initial analysis of the situation required significant resources in order to identify the root cause. An initial step included a focused data analysis which included collecting and analyzing large amounts of data from specific sites where potentially affected instruments were located. This process required that accounts exhibiting flow cell failure syndromes be identified and data was collected and analyzed to discover patterns and a root cause.

However, this focused data analysis was a lengthy process including many sites that were not good candidates, long waiting times to receive field data (mail or field service engineer visit), extensive data management that included many data formats and incomplete or insufficient data sets. Thus, the focused data analysis was not the answer to the problem.

Another step included in-house experiments in an effort to reproduce the problem. These experiments tested factors independently and the effects of the instrument modifications were studied. A total of 24 in-house experiments were performed. However, the in-house experiments had issues. First, flow cell failure is a low-frequency event rendering it difficult to reproduce. High instrument usage was required to reproduce the issue which was time consuming and expensive. Further, variability in instruments, instrument operation, and blood samples contributed to experiment complexity and interfered with experiment standardization and produced inconclusive or statistically unreliable results. Thus, in-house experiments were unlikely to reproduce a highly complex and stochastic phenomenon such as a flow cell failure.

As a result of the focused data analysis and the in-house experiments, over 240 GB of data from more than 40 instruments were analyzed, over 170 GB of data from field visits were analyzed, and over 125,000 blood samples from 24 in-house experiments were performed. This analysis identified some potential root causes, but no statistically robust conclusions were drawn.

An initial solution to the above issues was developed. A database system was developed wherein a readily available database with vast amounts of near real-time data from instruments installed worldwide was utilized. The database solution included setting up a dedicated server that could handle big, rich data that catered to large-scale, complex investigations. Then, several programs were developed that worked in conjunction to enable efficient big data management and analysis. This database system can be utilized on various instruments and identify many different issues.

Figure 9:
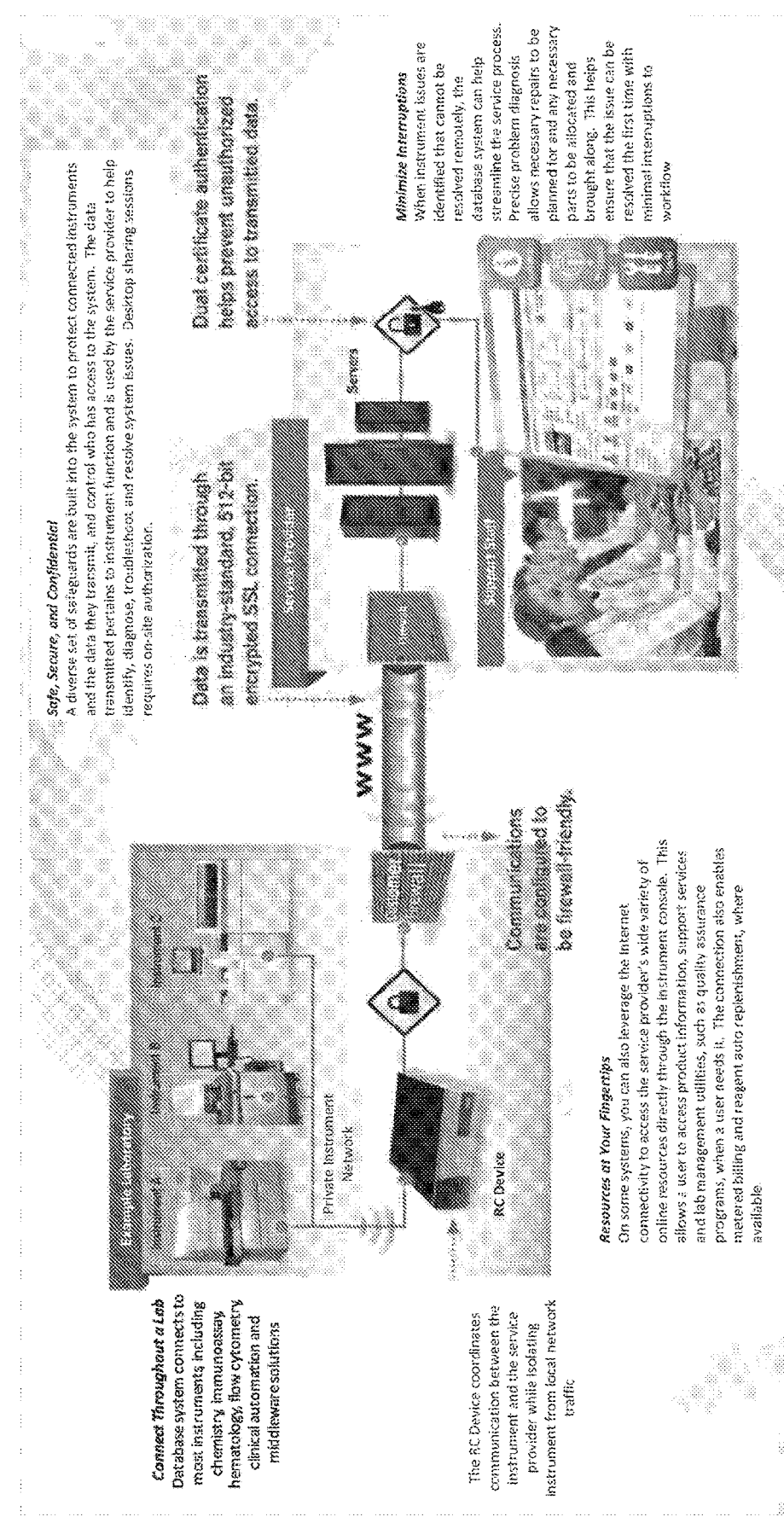
FIG. 9 is a high level schematic of an exemplary database system based on those shown in and described in relation to FIGS. 1, 2A and 2B.

This database system is a remote management and diagnostics system that allows for continuous transfer of analysis and performance data from instruments to remote servers or servers in control of the manufacturer or service provider. Incoming data may be channeled into a set of applications that enable the manufacturer or service provider to diagnose and help resolve instrument issues. An illustration of the database system is illustrated in FIG. 9.

The database system may provide an application interface or dashboard including system information on an instrument-by-instrument basis. The interface may allow the service provider's service and support to access near real-time system status, and track user-defined system parameters to trigger performance warnings.

In one embodiment, the dashboard may be fed by a remote data collection pipeline database loaded on the servers and stored in an Oracle (or other) database.

The database system was a potential solution to the limitations of the flow cell investigation. The early database system was readily available and provided information from approximately 1,600 instruments installed worldwide, an untapped data mine of trends representative of field behavior.

However, there still existed several challenges. These challenges included the fact that the original system was primarily designed for real-time monitoring of individual instruments, not for large-scale, high-dimensional data analysis over time. In other words, for large-scale, high-dimensional data analysis over time, data may need to be analyzed with more sophisticated statistical tools and downloaded locally in order to be analyzed.

For day to day use, it may be that less data will be used or maintained than would preferably be used for analysis of a stochastic phenomenon such as the flow cell related failures described herein. For example, it is possible that a person or entity desiring to perform analysis of a stochastic phenomenon may have deployed systems which store only three months of data, but this timeframe for data storage may not be sufficient to see trends in flow cell investigation. A big-data database may be able to store data for a large period of time, such as six months, one year, or other similar period. Thus, in this type of situation, to overcome the three-month data limit of an existing database, a big-data server could be set up to store one year of instrument data.

But, a big-data database may pose further challenges. Data in a big-data database may need to be stored in a local computer for analysis. However, transferring such large data sets may take significant time and bandwidth, bandwidth which may be sufficient to shut down a call center. Data transferred from big-data database may be so large that no local computer could handle it. For example, Tables 2 and 3 illustrate the mass of data that was encountered.

TABLE 2 exemplary three-month data set metrics

| Table | Records | Instruments |
| --- | --- | --- |
| Sample Data | 19,210,430 | 1,567 |
| Event Log | 16,956,114 | 1,624 |
| Daily Check | 221,226 | 1,609 |
| VCS Latron | 189,541 | 1,565 |

TABLE 3 exemplary one-year big-data data set metrics

| Table | Records | Memory | Instruments |
| --- | --- | --- | --- |
| Sample Data | 68,708,571 | 69.1 GB | 1,873 |
| Event Log | 48,620,946 | 18.7 GB | 1,858 |
| Daily Check | 729,449 | 1.1 GB | 1,855 |
| VCS Latron | 663,956 | 532 MB | 1,840 |

Some solutions that were investigated included: computer processor/memory upgrades; develop specific programs developed in C#, R, MATLAB, and JMP Statistical Software; and work in conjunction and efficiently to load, manage, standardize, and graphically represent data. Ultimately, a combination of multiple solutions proved effective, with upgraded hardware used to process data which was cross linked using translation tables to correlate data from individual records and reduce the amount of information that had to be stored in RAM or communicated at any one time.

Figure 10:
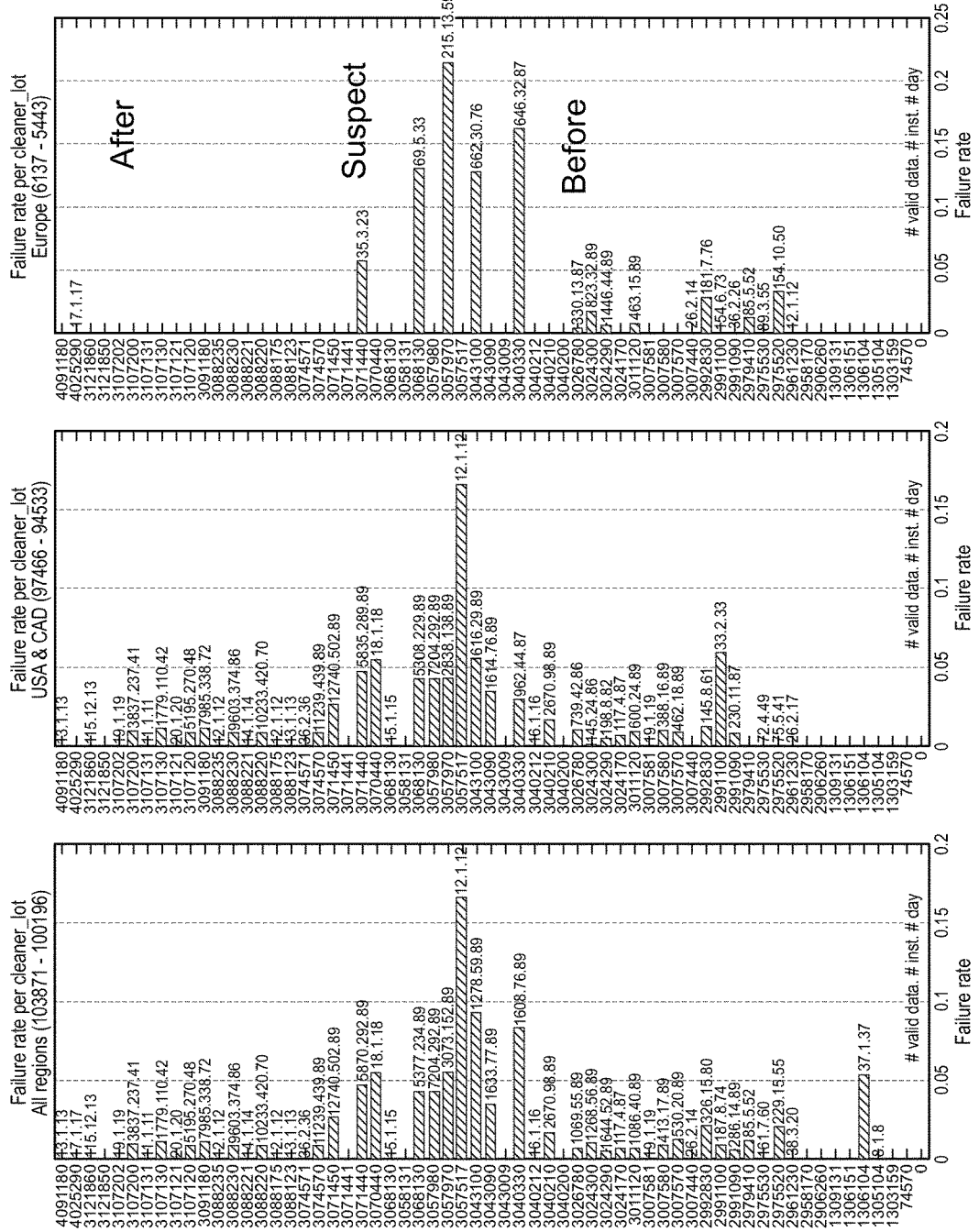
FIG. 10 is a screenshot of an exemplary embodiment of an application produced from database systems such as FIGS. 1, 2A, 2B, and 9.

Analysis of 1-year data revealed 2 of 3 primary drivers for increase in instrument flow cell failures. A first driver was a reduction in effectiveness of certain lots of instrument cleaner. The loss in effectiveness of instrument cleaner lots correlated with a single lot of raw material, which was different from other lots that performed satisfactorily. External analysis of flow cell walls showed debris of urea and sulfate (from degraded hemoglobin protein and antimicrobials) which the instrument cleaner was not effective in removing. FIG. 10 illustrates failure rate indicated by bar height, per cleaner lot, per region. As illustrated, once the lots were replaced, failure decreased.

A second driver was a reduction of functionality of the auto-purge cycle in a particular version of instrument software. In a previous software version, the flow cell aperture was backflushed up to 3 times in the presence of full clogs, whereas in the newer software, the flow cell was only backflushed twice.

Corrective measures were taken after the drivers were identified using the database system. Data for corrective measures are in Table 4.

TABLE 4

| | Counter Measure | Counter Measure Start Date | Benefit Realization | Impact | Comments |
| --- | --- | --- | --- | --- | --- |
| 1 | Flow cell purge with cleaner | First day | Immediate | 0.10-0.15 | There has been a reduction in the rate during this time but it is not clear if the reduced use of the suspect cleaner lots or the implementation of the new cleaner lots is the primary driver for improvements. |

TABLE 4-continued

| | Counter Measure | Counter Measure Start Date | Benefit Realization | Impact | Comments |
|---|---|---|---|---|---|
| 2 | Probe surface finish | First month | Shipped in new products since start date and available as needed upon failure | 0.18-0.27 | Differences from flat versus sharp probes will reduce coring in the system. The reduction in coring is obvious and will have an reducing error impact, but it is difficult to enumerate. |
| 3 | Cleaner | Third month | Within a month or so, all suspect cleaning lots will no longer be in use as new lots will be available | ~1.5 | 35-55% reduction in error rate seen at its peak. Until confirmation and root cause of the cleaner failure, this estimate is based on a transient failure that the recall will correct and assumes the ECS rate associated with the flow cell clogs does not include any HgB or bleaching issues. |
| 4 | Software purge | Fourth month outside US, Second day in US | Over time as software is updated in field. | 0.05-0.15 | Autopurge was seen to be successful in 1 of 12 instances in which there were three consecutive failures. |

The corrective measures with the most benefit included: defective cleaner lots were identified, placed in stop shipment, and recalled and a refined cleaning cycle was reintegrated into new software releases.

This case study shows that a data analytics program or module, when applied to large amounts of rich data, e.g., a big-data data set, may provide solutions to stochastic phenomenon that would otherwise not be evident from analyzing the failure of a single instrument.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

What is claimed is:

1. A system comprising:
a plurality of remote analytical instruments operably coupled to one or more servers, wherein each of the plurality of remote analytical instruments is configured to transmit measurement data for storage in one or more repositories on the one or more servers,
one or more processors associated with the one or more servers, wherein the one or more processors are configured to perform acts comprising:
storing measurement data transmitted from the plurality of remote analytical instruments in the one or more repositories along with corresponding metadata;
retrieving measurement data transmitted from the plurality of remote analytical instruments;
using the metadata, correlating measurement data from a first remote analytical instrument with measurement data from a second remote analytical instrument; and
identifying a potential driver for a stochastic phenomenon based on comparing the correlated measurement data from the first and second remote analytical instruments.

2. The system of claim 1, wherein:
comparing the correlated measurement data from the first and second remote analytical instruments comprises comparing:
a number of samples of a particular type of fluid tested on the first remote analytical instrument during a time period; and
a number of samples of the particular type of fluid tested on the second remote analytical instrument during the time period;
identifying the potential driver for the stochastic phenomenon comprises identifying a workflow imbalance between the first remote analytical instrument and the second remote analytical instrument in tests performed on the particular type of fluid; and
the one or more processors are further configured to generate a remediation comprising balancing the workflow between the first remote analytical instrument and the second remote analytical instrument in tests performed on the particular type of fluid.

3. The system of claim 1, wherein the acts the one or more processors are configured to perform comprise:
maintaining consumable usage data for each of the plurality of remote analytical instruments; and
in response to a request from a user associated an instrument from the plurality of instruments, providing the user with a report of consumables on the instrument.

4. The system of claim 1, wherein:
the plurality of remote analytical instruments comprises a first set of remote analytical instruments associated with a first entity, and a second set of remote analytical instruments associated with a second entity; and
the plurality of acts the one or more processors are configured to perform comprise:
using data from instruments comprising the first set of remote analytical instruments and the second set of remote analytical instruments to identify, and determine a plurality of solutions to, a problem on an instrument from the first set of remote analytical instruments; and
presenting a user associated with the first set of remote analytical instruments with a ranked list of the plurality of solutions to the problem on the instrument from the first set of remote set of analytical instruments.

5. The system of claim 1, wherein the plurality of acts the one or more processors are configured to perform comprise:
determining a threshold for a reagent on an instrument from the plurality of instruments based on reagent consumption data from the one or more repositories and a projection of workload for the instrument over for a future duration;
performing a comparison of a level of the reagent at the instrument with the threshold; and
based on the comparison, performing an act from a group consisting of:
generating an inventory ticket for a manager of a laboratory where the instrument is located; and
generating an order for the reagent for a supplier of the reagent.

6. The system of claim 1, wherein:
each instrument from the plurality of remote analytical instruments comprises a rich data generation module adapted to provide the measurement data with one or more of associated tag information items from a group consisting of:
lot and serial number information for calibrators, controls and reagents;
calibration results,
control results,
assay parameters used to generate results,
sample type, description and container type,
sample quality indices generated by instrument users,
underlying raw result data,
non-HIPAA sample specific information identified as potentially impacting a test result; and
maintenance and service records,
and
the acts the one or more processors are configured to perform comprise providing support for:
the plurality of remote analytical instruments; and
assays run on the plurality of remote analytical instruments;
by performing data mining with the tag information items from the data generation modules of the plurality of remote analytical instruments.

7. The system of claim 1, wherein:
the system comprises the one or more repositories; and
the acts the one or more processors are configured to perform comprise:
receiving a search query; and
executing the search query against the one or more repositories based on relating data from a first instrument from the plurality of remote analytical instruments with data from a second instrument from the plurality of remote analytical instruments using one or more tables comprising metadata associated with data from the first and second instruments.

8. The system of claim 1, wherein identifying the potential driver for the stochastic phenomenon comprises using:
data stored in the one or more repositories; and
translation tables which reduce the amount of data required to be stored in random access memory for analysis by an analytics module.

9. The system of claim 1, wherein:
each instrument from the plurality of remote analytical instruments is configured to transmit quality control data indicating quality control measurements run on that instrument;
the plurality of remote analytical instruments comprises a first set of remote analytical instruments associated with a first entity, and a second set of remote analytical instruments associated with a second entity; and
the plurality of acts the one or more processors are configured to perform comprise:
identifying the first set of remote analytical instruments as a peer group of the second set of remote analytical instruments;
performing a statistical analysis of quality control data from the first set of remote analytical instruments and the second set of remote analytical instruments; and
in response to a request from a user associated with the first set of remote analytical instruments, providing a report comprising a result of the statistical analysis.

10. The system of claim 1, wherein:
the plurality of remote analytical instruments comprises a plurality of sets of remote analytical instruments;
the system comprises a plurality of remote communication devices, wherein each remote communication device from the plurality of remote communication devices is:
located at a corresponding laboratory where a set of remote analytical instruments is also located; and
is configured to encrypt data from the set of remote analytical instruments which is also located at the corresponding laboratory and transmit it for storage in the one or more repositories;
and
the one or more servers host a remote diagnostics application adapted to provide a dashboard providing real time data regarding instruments located at a specified laboratory in response to a user request.

11. The system of claim 1, wherein the stochastic phenomenon is a phenomenon which is unpredictable because of the influence of one or more externally determined variables.

12. A method of diagnosing analytical instruments, the method comprising:
collecting, into at least one or more repositories, data from a plurality of remote analytical instruments along with corresponding metadata;
retrieving measurement data transmitted from the plurality of remote analytical instruments;
using the metadata, correlating measurement data from a first remote analytical instrument with measurement data from a second remote analytical instrument; and
identifying a potential driver for a stochastic phenomenon based on comparing the correlated measurement data from the first and second remote analytical instruments.

13. The method of claim 12, wherein:
comparing the correlated measurement data from the first and second remote analytical instruments comprises comparing:
a number of samples of a particular type of fluid tested on the first remote analytical instrument during a time period; and
a number of samples of the particular type of fluid tested on the second remote analytical instrument during the time period;
identifying the potential driver for the stochastic phenomenon comprises identifying a workflow imbalance between the first remote analytical instrument and the second remote analytical instrument in tests performed on the particular type of fluid; and
the method comprises generating a remediation comprising balancing the workflow between the first remote analytical instrument and the second remote analytical instrument in tests performed on the particular type of fluid.

14. The method of claim 12, wherein the method comprises:
maintaining consumable usage data for each of the plurality of remote analytical instruments; and
in response to a request from a user associated an instrument from the plurality of instruments, providing the user with a report of consumables on the instrument.

15. The method of claim 12, wherein:
the plurality of remote analytical instruments comprises a first set of remote analytical instruments associated with a first entity, and a second set of remote analytical instruments associated with a second entity; and
the method comprises:
using data from instruments comprising the first set of remote analytical instruments and the second set of remote analytical instruments to identify, and determine a plurality of solutions to, a problem on an instrument from the first set of remote analytical instruments; and
presenting a user associated with the first set of remote analytical instruments with a ranked list of the plurality of solutions to the problem on the instrument from the first set of remote set of analytical instruments.

16. The method of claim 12, wherein the method comprises:
determining a threshold for a reagent on an instrument from the plurality of instruments based on reagent consumption data from the one or more repositories and a projection of workload for the instrument over for a future duration;
performing a comparison of a level of the reagent at the instrument with the threshold; and
based on the comparison, performing an act from a group consisting of:
generating an inventory ticket for a manager of a laboratory where the instrument is located; and
generating an order for the reagent for a supplier of the reagent.

17. The method of claim 12, wherein:
each instrument from the plurality of remote analytical instruments comprises a rich data generation module adapted to provide the measurement data with one or more of associated tag information items from a group consisting of:
lot and serial number information for calibrators, controls and reagents;
calibration results,
control results,
assay parameters used to generate results,
sample type, description and container type, sample quality indices generated by instrument users,
underlying raw result data,
non-HIPAA sample specific information identified as potentially impacting a test result; and
maintenance and service records,
and
the method comprises providing support for:
the plurality of remote analytical instruments; and
assays run on the plurality of remote analytical instruments;
by performing data mining with the tag information items from the data generation modules of the plurality of remote analytical instruments.

18. The method of claim 12, wherein the method comprises:
receiving a search query; and
executing the search query against the one or more repositories based on relating data from a first instrument from the plurality of remote analytical instruments with data from a second instrument from the plurality of remote analytical instruments using one or more tables comprising metadata associated with data from the first and second instruments.

19. The method of claim 12, wherein identifying the potential driver for the stochastic phenomenon is based on:
data stored in the one or more repositories; and
translation tables which reduce the amount of data required to be stored in random access memory for analysis by an analytics module.

20. The method of claim 12, wherein:
each instrument from the plurality of remote analytical instruments is configured to transmit quality control data indicating quality control measurements run on that instrument;
the plurality of remote analytical instruments comprises a first set of remote analytical instruments associated with a first entity, and a second set of remote analytical instruments associated with a second entity; and
the method comprises:
identifying the first set of remote analytical instruments as a peer group of the second set of remote analytical instruments;
performing a statistical analysis of quality control data from the first set of remote analytical instruments and the second set of remote analytical instruments; and
in response to a request from a user associated with the first set of remote analytical instruments, providing a report comprising a result of the statistical analysis.

21. The method of claim 12, wherein:
the plurality of remote analytical instruments comprises a plurality of sets of remote analytical instruments, each of which sets of remote analytical instruments is located at a corresponding laboratory; and
the method comprises providing a dashboard providing real time data regarding instruments located at a specified laboratory in response to a user request.

22. The method of claim 12, wherein the stochastic phenomenon is a phenomenon which is unpredictable because of the influence of one or more externally determined variables.

* * * * *